(12) United States Patent
Kim et al.

(10) Patent No.: US 9,186,502 B2
(45) Date of Patent: Nov. 17, 2015

(54) TREATMENT OF EXCESS WEIGHT BY NEURAL DOWNREGULATION IN COMBINATION WITH COMPOSITIONS

(75) Inventors: Dennis Dong-Won Kim, La Jolla, CA (US); Mark B. Knudson, Shoreview, MN (US)

(73) Assignee: EnteroMedics Inc., St. Paul, MN (US)

( * ) Notice: Subject to any disclaimer, the term of this patent is extended or adjusted under 35 U.S.C. 154(b) by 657 days.

(21) Appl. No.: 12/370,984

(22) Filed: Feb. 13, 2009

(65) Prior Publication Data

US 2009/0210019 A1 Aug. 20, 2009

Related U.S. Application Data

(60) Provisional application No. 61/028,691, filed on Feb. 14, 2008.

(51) Int. Cl.
| | | |
|---|---|---|
| *A61N 1/05* | (2006.01) | |
| *A61N 1/36* | (2006.01) | |
| *A61M 5/142* | (2006.01) | |
| *A61N 1/372* | (2006.01) | |

(52) U.S. Cl.
CPC ........ *A61N 1/36007* (2013.01); *A61M 5/14276* (2013.01); *A61M 2205/353* (2013.01); *A61M 2205/3515* (2013.01); *A61M 2205/3523* (2013.01); *A61M 2210/105* (2013.01); *A61M 2210/1053* (2013.01); *A61N 1/36114* (2013.01); *A61N 1/37264* (2013.01)

(58) Field of Classification Search
CPC ........... A61N 1/36053; A61N 1/36085; A61N 1/0568; A61N 1/36007

USPC .................. 607/2–3, 9, 40, 58–59
See application file for complete search history.

(56) References Cited

U.S. PATENT DOCUMENTS

| | | |
|---|---|---|
| 6,243,607 B1 | 6/2001 | Mintchev et al. |
| 6,449,511 B1 | 9/2002 | Mintchev et al. |
| 6,928,320 B2 | 8/2005 | King |
| 7,167,750 B2 | 1/2007 | Knudson et al. |
| 7,343,201 B2 | 3/2008 | Mintchev |

(Continued)

FOREIGN PATENT DOCUMENTS

| | | |
|---|---|---|
| EP | 0 896 828 A2 | 2/1999 |
| WO | WO 2004/036377 A2 | 4/2004 |

(Continued)

OTHER PUBLICATIONS

Camilleri, M. et al., "Selection of electrical algorithms to treat obesity with intermittent vagal block using an implantable medical device," *Surgery for Obesity and Related Diseases*, vol. 5, pp. 224-230 (2009).

(Continued)

*Primary Examiner* — Christopher D Koharski
*Assistant Examiner* — Michael Carey
(74) *Attorney, Agent, or Firm* — Merchant & Gould, P.C.

(57) ABSTRACT

A method and system for designing a therapy or for treating a condition associated with excess weight in a subject comprising applying a neural conduction block to the vagus nerve at a blocking site with the neural conduction block selected to at least partially block nerve impulses on the vagus nerve at the blocking site and administering a composition comprising an effective amount of an agent that alters the energy balance of the subject.

5 Claims, 16 Drawing Sheets

(56) References Cited

U.S. PATENT DOCUMENTS

| | | | |
|---|---|---|---|
| 7,444,183 B2 | 10/2008 | Knudson et al. | |
| 7,489,969 B2 | 2/2009 | Knudson et al. | |
| 7,620,454 B2 | 11/2009 | Dinsmoor et al. | |
| 7,620,455 B2 | 11/2009 | Maschino | |
| 7,720,539 B2 | 5/2010 | Mintchev | |
| 8,239,027 B2 | 8/2012 | Imran | |
| 8,260,426 B2 | 9/2012 | Armstrong et al. | |
| 2004/0172085 A1 | 9/2004 | Knudson et al. | |
| 2004/0172086 A1 | 9/2004 | Knudson et al. | |
| 2004/0172088 A1 | 9/2004 | Knudson et al. | |
| 2004/0176812 A1* | 9/2004 | Knudson et al. | 607/40 |
| 2004/0230255 A1* | 11/2004 | Dobak, III | 607/58 |
| 2005/0021101 A1* | 1/2005 | Chen et al. | 607/40 |
| 2005/0038484 A1 | 2/2005 | Knudson et al. | |
| 2005/0131485 A1 | 6/2005 | Knudson et al. | |
| 2006/0036293 A1 | 2/2006 | Whitehurst et al. | |
| 2006/0161217 A1* | 7/2006 | Jaax et al. | 607/40 |
| 2006/0229685 A1 | 10/2006 | Knudson et al. | |
| 2007/0043400 A1 | 2/2007 | Donders et al. | |
| 2007/0043411 A1 | 2/2007 | Foster et al. | |
| 2007/0135846 A1 | 6/2007 | Knudson et al. | |
| 2007/0135856 A1 | 6/2007 | Knudson et al. | |
| 2007/0135857 A1 | 6/2007 | Knudson et al. | |
| 2007/0135858 A1 | 6/2007 | Knudson et al. | |
| 2007/0142870 A1 | 6/2007 | Knudson et al. | |
| 2007/0198063 A1* | 8/2007 | Hunter et al. | 607/3 |
| 2007/0233193 A1 | 10/2007 | Craig | |
| 2007/0239226 A1 | 10/2007 | Overstreet | |
| 2008/0021512 A1 | 1/2008 | Knudson et al. | |
| 2008/0103533 A1* | 5/2008 | Patel et al. | 607/2 |
| 2008/0221644 A1 | 9/2008 | Vallapureddy et al. | |
| 2008/0281365 A1 | 11/2008 | Tweden et al. | |
| 2008/0300654 A1 | 12/2008 | Lambert et al. | |
| 2008/0300656 A1 | 12/2008 | Donders et al. | |
| 2008/0300657 A1 | 12/2008 | Stultz | |
| 2009/0187230 A1 | 7/2009 | Dilorenzo | |
| 2009/0275997 A1 | 11/2009 | Faltys et al. | |
| 2009/0306465 A1 | 12/2009 | Dudai | |
| 2010/0241183 A1 | 9/2010 | DiLorenzo | |
| 2010/0292754 A1* | 11/2010 | Gliner | 607/45 |
| 2011/0130804 A1 | 6/2011 | Lin et al. | |
| 2012/0022608 A1 | 1/2012 | Libbus et al. | |
| 2012/0022617 A1 | 1/2012 | Tockman et al. | |
| 2012/0053653 A1 | 3/2012 | Hiernaux et al. | |
| 2012/0059431 A1 | 3/2012 | Williams et al. | |
| 2012/0065698 A1 | 3/2012 | Errico et al. | |
| 2012/0071946 A1 | 3/2012 | Errico et al. | |
| 2012/0078319 A1 | 3/2012 | De Ridder | |
| 2012/0083855 A1 | 4/2012 | Gross et al. | |
| 2012/0101874 A1 | 4/2012 | Ben-Haim et al. | |
| 2012/0136408 A1 | 5/2012 | Grill et al. | |
| 2012/0232610 A1 | 9/2012 | Soffer et al. | |
| 2012/0239108 A1 | 9/2012 | Foutz et al. | |
| 2012/0253378 A1 | 10/2012 | Makower et al. | |
| 2012/0259380 A1 | 10/2012 | Pyles | |

FOREIGN PATENT DOCUMENTS

| | | |
|---|---|---|
| WO | WO 2004/110551 A2 | 12/2004 |
| WO | WO 2006/023498 A1 | 3/2006 |
| WO | WO 2009/131639 | 10/2009 |
| WO | 2012044472 A2 | 4/2012 |
| WO | 2012060874 A2 | 5/2012 |

OTHER PUBLICATIONS

Camilleri, M. et al., "Intra-abdominal vagal blocking (VBLOC therapy): Clinical results with a new implantable medical device," *Surgery*, vol. 143, No. 6, pp. 723-731 (Jun. 2008).

Camilleri, M. et al., "Vagal Blocking for Obesity Control (Vbloc): Plasma Pancreatic Polypeptide (PPP) Response to a Standardized Sham Meal Challenge," *Obesity*, vol. 15, Supplement, Abstract No. 20-OR, pp. A6-A7 (Sep. 2007).

Herrera et al., *Obesity Surgery* 18:946 (2008).

Kow et al., *Obesity Surgery*, 18:924 (2008).

Kow et al., *Obesity Surgery*, 18:914 (2008).

Toouli, J. et al., "Intra-Abdominal Vagal Blocking Reduces Calorie Intake, Enhances Satiation and Reduces Hunger During Significant and Sustained Weight Loss," *Gastroenterology*, vol. 134, No. 4, Suppl. 1, Abstract No. M1255, p. A-370, (Apr. 2008).

Toouli, J. et al., "Vagal blocking for obesity control (VBLOC): Effects on excess weight loss, calorie intake, satiation and satiety," *Obesity Surgery*, vol. 17, Abstract No. 83, p. 1043 (2007).

Tweden, K. et al., "Vagal Blocking for Obesity Control (VBLOC): Concordance of Effects of Very High Frequency Blocking Current at the Neural and Organ Levels Using Two Preclinical Models," *Gastroenterology*, vol. 130, No. 4, Suppl. 2, Abstract No. 951, p. A-148 (Apr. 2006).

Tweden et al., *Obesity Surgery* (2006) 16:988.

Wilson, R. et al., "Intra-Abdominal Vagal Blocking Reduces Body Weight with Associated Reductions in Heart Rate and Without Adverse Effects on Electrocardiographic Parameters," *Obesity Surgery*, vol. 18, Abstract No. 053, p. 923 (2008).

International Search Report and Written Opinion mailed May 25, 2009.

GenBank: AAA20828.1, Aug. 16, 1994, printed May 5, 2009, 2 pages.

GenBank: AAA35524.1, Mar. 1, 1994, printed May 5, 2009, 2 pages.

GenBank: AAA60140.1, Jan. 8, 1995, printed May 5, 2009, 2 pages.

GenBank: AAA60565.1, Jan. 13, 1995, printed May 5, 2009, 2 pages.

GenBank: AAB31818.1, Jan. 25, 1995, printed May 5, 2009, 2 pages.

GenBank: AAQ89412.1, Oct. 3, 2003, printed May 5, 2009, 2 pages.

GenBank: BAA09787.1, Aug. 18, 2007, printed May 5, 2009, 2 pages.

GenBank: CAA43009.1, Nov. 14, 2006, printed May 5, 2009, 2 pages.

NCBI Reference Sequence: NP_000221.1, Apr. 26, 2009, printed May 5, 2009, 4 pages.

NCBI Reference Sequence: NP_000406.1, Mar. 22, 2009, printed May 5, 2009, 5 pages.

NCBI Reference Sequence: NP_001515.1, Apr. 19, 2009, printed May 5, 2009, 5 pages.

NCBI Reference Sequence: NP_004151.2, Mar. 1, 2009, printed May 5, 2009, 4 pages.

Swiss-Prot: P01275.3, Mar. 3, 2009, printed May 5, 2009, 9 pages.

Swiss-Prot: P26441.1, Mar. 3, 2009, printed May 5, 2009, 5 pages.

Swiss-Prot: P32239.1, Mar. 3, 2009, printed May 5, 2009, 11 pages.

Swiss-Prot: P41837.1, Nov. 4, 2008, printed May 5, 2009, 2 pages.

Allison, D. et al., "Annual Deaths Attributable to Obesity in the United States," *JAMA*, vol. 282, No. 16, pp. 1530-1538 (Oct. 27, 1999).

Barinaga, M., "New Appetite-Boosting Peptides Found," *Science*, vol. 279, No. 5354, 2 pages (Feb. 20, 1998).

Chaput, J. et al., "Current and novel approaches to the drug therapy of obesity," *Eur. J. Clin. Pharmacol*, vol. 62, pp. 793-803 (2006).

Clinical Guidelines on the Identification, Evaluation, and Treatment of Overweight and Obesity in Adults, The Evidence Report, *National Institutes of Health*, NIH Publication No. 98/4083, Chapters 2-4, 95 pages (Sep. 1998).

Fahimian, N., "Modern Trends in Managing Obesity—Evolution of a New Drug: Sibutramine (MERIDIA TM)," *Nutrition Bytes*, vol. 4, No. 2, 5 pages (1998).

Fontaine, K. et al., "Years of Life Lost Due to Obesity," *JAMA*, vol. 289, No. 2, pp. 187-193 (Jan. 8, 2003).

Gershon, "The Second Brain," *Harper Collins Publisher, Inc.*, New York, N.Y., p. 19 (1998).

Inui, A., "Ghrelin: An orexigenic and somatotrophic signal from the stomach," *Nature Reviews*, vol. 2, pp. 1-10 (Aug. 2001).

Jenkins, T., "Prevalence of Overweight, Obesity, and Comorbid Conditions Among U.S. and Kentucky Adults, 2000-2002," *Preventing Chronic Disease*, vol. 2, No. 1, 10 pages (Jan. 2005).

Kilgore, K. et al., ."Nerve conduction block utilising high-frequency alternating current," *Medical & Biological Engineering & Computing*, vol. 42, pp. 394-406 (2004).

Mokdad, A. et al., "The Spread of the Obesity Epidemic in the United States, 1991-1998," *JAMA*, vol. 282, No. 16, pp. 1519-1522 (Oct. 27, 1999).

(56) References Cited

OTHER PUBLICATIONS

Rosen, E. et al., "Molecular Regulation of Adipogenesis," *Annual Review of Cell and Developmental Biology*, vol. 16, pp. 145-171 (2000).

Solomonow, M. et al., "Control of muscle contractile force through indirect high-frequency stimulation," *American Journal of Physical Medicine*, vol. 62, No. 2, pp. 71-82 (1983).

The Surgeon General's Call to Action to Prevent and Decrease Overweight and Obesity 2001, *U.S. Department of Health and Human Services*, 39 pages (2001).

Toshinai, K. et al., "Upregulation of Ghrelin Expression in the Stomach upon Fasting, Insulin-Induced Hypoglycemia, and Leptin Administration," *Biochemical and Biophysical Research Communications*, vol. 281, pp. 1220-1225 (2001).

Herrera, Miguel F., et al., "Intermittent Vagal Blocking with an Implantable Device Reduces Maximum Tolerated Volume (MTV) During a Standardized Nutrient Drink Test in Obese Subjects," AGA Institute, AASLD, SSAT, The 110th Annual Meeting of the AGA Institute: Digestive Disease Week May 30-Jun. 4, 2009, Chicago, IL, Gastroenterology vol. 136, No. 5, Suppl. 1 (May 2009).

Brancatisano, R., et al., "Implantation Technique of a Novel Vagal Blockade Medical Device for the Treatment of Obesity," IFSO-APC OSSANZ Conference 2008: Mar. 25-27, 2009, Hilton Cairns, Queensland Conference Program Handbook.

Toouli, M.D., James, et al., "Intra-Abdominal Vagal Blocking Reduces Calorie Intake, Enhances Satiation and Reduces Hunger during Significant and Sustained Weight Loss in Obese Subjects," Digestive Disease Week and the 109th Annual Meeting of the AGA Institute: May 17-22, 2008, San Diego, CA, Gastroenterology vol. 134, No. 4 (Suppl. 1) p. A-370 (Apr. 2008).

Tweden, Katherine S., et al. "Vagal Blocking for Obesity Control (VBLOC): Studies of Pancreatic Function and Safety in a Porcine Model," Obesity Surgery: Including Laparoscopy and Allied Care, Program Issue, World Congress, Australia, Aug. 30-Sep. 2, 2006. An International Surgical Journal for Research and Treatment of Massive Obesity, vol. 16, No. 8, p. 988, Aug. 2006.

Toouli, M.D., James, et al., "Vagal Blocking for Obesity Control (VBLOC): Effects on Excess Weight Loss, Calorie Intake, Satiation and Satiety," Obesity Surgery: Including Laparoscopy and Allied Care, Program Issue, World Congress, Porto, Sep. 5-8, 2007. An International Surgical Journal for Research and Treatment of Massive Obesity, vol. 17, No. 8, p. 1043 Aug. 2007.

Kow, M.D., Lilian, et al., "Comparison of Food Ingestion Disorders with Three Devices for Obesity," Obesity Surgery: Including Laparoscopy and Allied Care, Program and Abstracts of the 13th World Congress of IFSO, Buenos Aires, Argentina, Sep. 24-27, 2008. An International Surgical Journal for Research and Treatment of Massive Obesity, vol. 18, No. 8, pp. 914-915 Aug. 2008.

Wilson, R.R., et al., "Intra-Abdominal Vagal Blocking Re3duces body Weight with Associated Reductions in Heart Rate and Without Adverse Effects on Electrocardiographic Parameters," Obesity Surgery: Including Laparoscopy and Allied Care, Program and Abstracts of the 13th World Congress of IFSO, Buenos Aires, Argentina, Sep. 24-27, 2008. An International Surgical Journal for Research and Treatment of Massive Obesity, vol. 18, No. 8, p. 923 Aug. 2008.

Kow, M.D., Lilian, et. al. "Selecting Vagal Blocking Electrical Algorithms for Obesity Treatment," Obesity Surgery: Including Laparoscopy and Allied Care, Program and Abstracts of the 13th World Congress of IFSO, Buenos Aires, Argentina, Sep. 24-27, 2008. An International Surgical Journal for Research and Treatment of Massive Obesity, vol. 18, No. 8, p. 924, Aug. 2008.

Herrera, Miguel F., et al., "VBLOC and Improvements in Co-Morbidities in Obese Subjects During Weight Loss," Obesity Surgery: The Journal of Metabolic Surgery and Allied Care, Program and Abstracts of the 14th World Congress of IFSO, Paris, France, Aug. 26-29, 2009. An International Surgical Journal for Research and Treatment of Massive Obesity, vol. 19, No. 8, p. 983-984, Aug. 2009.

Herrera, Miguel F., et al., "Intermittent Vagal Blocking with an Implantable Device Reduces Maximum Tolerated Volume (MTV) During a Standardized Nutrient Drink Test in Obese Subjects," Obesity Surgery: The Journal of Metabolic Surgery and Allied Care, Program and Abstracts of the 14th World Congress of IFSO, Paris, France, Aug. 26-29, 2009. An International Surgical Journal for Research and Treatment of Massive Obesity, vol. 19, No. 8, p. 1012 Aug. 2009.

Brancastisano, Roy, et al., "Empower: A 12-Month Randomized, Prospective Clinical Trial: Safety and Effectiveness of VBLOC Therapy," 23rd Annual Scientific Conference of the Obesity Surgery Society of Australia and New Zealand, OSSANZ Conference 2010: The Changing Shape of Bariatrics, Nov. 10-12, Wednesday Nov. 10 10:30 am-12 noon, Tasmania Hotel Grand Chancellor, Hobart, Conference Program Handbook.

Kow, M.D., Lilian, et al., "Vagal Blocking Improves Obesity-Related Co-Morbidities in Obese Subjects with type 2 Diabetes Mellitus," 23rd Annual Scientific Conference of the Obesity Surgery Society of Australia and New Zealand , OSSANZ Conference 2010: The Changing Shape of Bariatrics, Nov. 10-12, Wednesday Nov. 10 3:30 pm-5:00 pm, Tasmania Hotel Grand Chancellor, Hobart, Conference Program Handbook.

Collins, Jane, et al., "Reduces Calorie Intake and Weight Loss during Vagal Block (VBLOC Therapy) in Morbidly Obese Patients with Type 2 Diabetes Mellitus," 23rd Annual Scientific Conference of the Obesity Surgery Society of Australia and New Zealand, OSSANZ Conference 2010: The Changing Shape of Bariatrics, Nov. 10-12, Thursday Nov. 11 10:30 am-12 noon, Tasmania Hotel Grand Chancellor, Hobart, Conference Program Handbook.

Toouli, M.D., James, et al., "Vagal Blocking: Treatment of Obesity Related type 2 Diabetes and blood Pressure—18 Month Results," 24th Annual Scientific Conference of the Obesity Surgery Society of Australia and New Zealand, OSSANZ Conference 2012: Bariatric surgery-more than an operation, Apr. 11-13, Wednesday Nov. 11 3:30 pm-5:00 pm, Northern Territory Darwin Convention Centre, Darwin, Conference Program Handbook.

Tweden, Katherine S., et al., "Vagal Blocking for Obesity Control (VBLOC): Studies of Pancreatic and Gastric Function and Safety in a Porcine Model," Plenary Session 2006/2 Surgery for Obesity and Related Diseases, Official Journal of the American Society for Bariatric Surgery, vol. 2, No. 3, pp. 301-302, May/Jun. 2006.

Camilleri, M.D., Michael, et al., "Selection of Electrical Algorithms to Treat Obesity with Intermittent Vagal Block Using an Implantable Medical Device," Surgery for Obesity and Related Diseases, Official Journal of the American Society for Bariatric Surgery, vol. 5, No. 2, pp. 224-229, Mar./Apr. (2009).

Herrera, Miguel F., et al., "Intermittent Vagal Blockade with an Implantable Device Improves Glycemic Control in Obese subjects with Type 2 Diabetes," 2009 Poster Session / Supplement to Surgery for Obesity and Related Diseases, Official Journal of the American Society for Bariatric Surgery, vol. 5, No. 3S, pp. S48-S49, May/Jun. (2009).

Herrera, Miguel F., et al., "Vagal Blocking Improves Glycemic Control and Blood Pressure in Subjects with Type 2 Diabetes and Hypertension," 2010 Plenary Session / Supplement to Surgery for Obesity and Related Diseases, Official Journal of the American Society for Bariatric Surgery, vol. 2, No. 3, pp. S1-S26, May/Jun. (2010).

Camilleri M.D., Michael, et al., "Vagal Blocking for Obesity control (VBLOC): Plasma Pancreatic Polypeptide (PPP) Response to a Standardized Sham Meal Challenge," The Obesity Society 2007 Annual Scientific Meeting, Oct. 20-24, 2007, New Orleans Louisiana. Supplement to Obesity, vol. 15, Program Abstract Supplement, Sep. (2007).

Camilleri, M.D., Michael, et al., "Intra-abdominal Vagal Blocking (VBLOC therapy): Clinical Results with a New Implantable Medical Device," Surgery, vol. 143, No. 6, pp. 723-731, Jun. 2008.

Kow, M.D., Lilian, et al., "Vagal Blocking for the Treatment of Obesity Delivered Using the Fully Implantable Maestro Rechargeable System: 12 Month Results," Surgery for Obesity and Related Diseases: Emerging Technologies Session 2011, 7, pp. 363-364, (2011).

Sarr, M.G., et al., "The EMPOWER Study: Randomized, Prospective, Double-Blind, Multicenter Trial of Vagal Blockade to Induce Weight Loss in Morbid Obesity," Obes. Surg. Published Sep. 8, 2012, (12pp) Springer Science+Business Media, LLC (2012).

(56) References Cited

OTHER PUBLICATIONS

Tweden, Katherine S., et al., "Vagal Blocking Treatment of Obesity Related Type 2 Diabetes and Blood Pressure—18 Month Results," 5th Congress of the International Federation for the surgery of Obesity and Metabolic Disorders European Chapter (IFSO-EC), Barcelona '12, Apr. 26-28, 2012.

Toouli, M.D., James, et al., "Vagal Blocking for Obesity Control (VBLOC): Interim Six Months Results in an ongoing Trial Using a Second Generation System," 2008 Scientific Session of the Society of American Gastrointestinal and Endoscopic (SAGES), Philadelphia, Pennsylvania, USA Apr. 9-12, 2008. Poster Presentations, Surgical Endoscopy (2008) 22, p. S194, Springer Science+Business Media, LLC (2008).

Toouli, M.D., James, et al., "Vagal Blocking for Obesity Control (VBLOCTM): Ongoing Comparison of Weight Loss with Two Generations of an Active, Implantable Medical Device," 2008 Plenary Session II / Surgery for Obesity and Related Diseases, Official Journal of the American Society for Bariatric Surgery, e t al., vol. 4, No. 3, p. 305, May/Jun. (2008).

Waataja, Jonathan J., et al., "Effects of High-Frequency Alternating Current on Axonal Conduction Through the Vagus Nerve," Journal of Neural Engineering Neural Eng. 8 (2011) (1741-1747) IOP Publishing Ltd, (2011) online at stacks.iop.org.

Kow, M.D., Lilian, et al., "Comparison of Food Ingestion disorders with Three Devices for Obesity Treatment," and Wilson, Richard, et al., "Intra-abdominal Vagal Blocking Reduces Body Weight with Associated Reductions in Heart Rate and Without Adverse Effects on Electrocardiographic Parameters," TOS 2008 Abstract Supplement / Poster Session 2 Abstracts, vol. 16, Supp. 1: S222, Oct. (2008) www.obesityjournal.org.

Herrera, Miguel F., et al., "Treatment of Obesity-Related Type 2 Diabetes with Vagal Blocking," Obesity 2011 Abstract Supplement / Poster Abstracts—Monday, Oct. 3, 2011, Obesity vol. 19, sup. 1:S185, Nov. 2011, www.obsesityjournal.org.

Wray, N., et al., "Reduced Calorie Intake and Weight Loss During Vagal Blocking in Subjects with Obesity-Related Type 2 Diabetes Mellitus," Obesity 2011 Abstract Supplement / Poster Abstracts— Monday, Oct. 3, 2011, Obesity vol. 19, Supp. 1:S190, Nov. 2011, www.obesityjournal.org.

Toouli, M.D., James, et al., "Reduced Calorie Intake and Weight Loss During Vagal Bloc (VBLOC Therapy) in Morbidly Obese Patients with Type 2 Diabetes Mellitus," Gastroenterology 2011, vol. 140: S-619, AGA Institute.

Tweden, Katherine S., et al., "Vagal Blocking for Obesity Control (VBLOC): Concordance of Effects of Very High Frequency Blocking Current at the Neural and Organ Levels Using Two Preclinical Models," Gastroenterology 2006, vol. 130 (suppl2 2) A-148, AGA Institute.

Kow, M.D., Lilian, et al., "An Implantable Vagal Blocking System to Treat Obesity: Laparoscopic Implantation Technique and Early Results in a proof-of-Principle Clinical Study," , SAGES 2008 Emerging Technology Oral Abstracts, p. 295, www.sages.org.

Toouli, M.D., James, et al., "Treatment of Obesity-Related Co-Morbidities with VBLOC Therapy," Obes. Surg. 21:998, Springer Science+Business Media, LLC (2011).

\* cited by examiner

FIG. 10
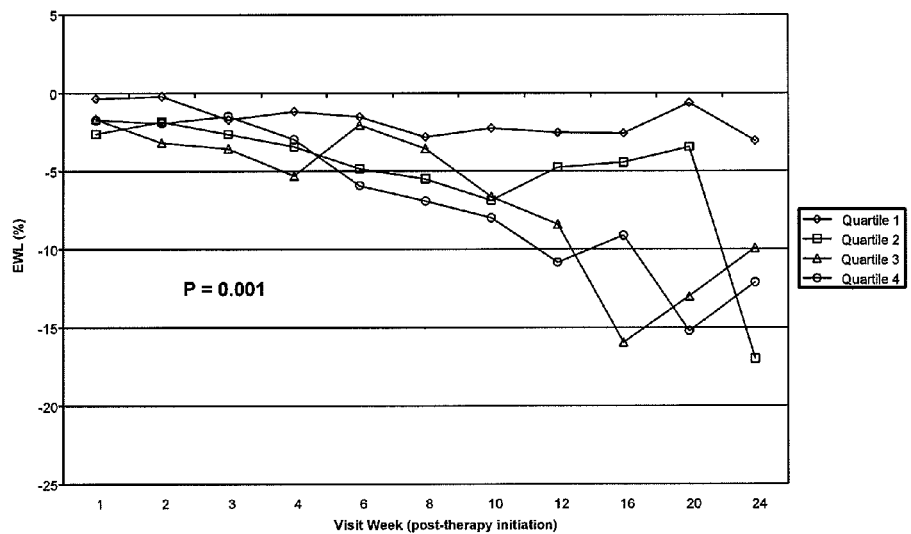
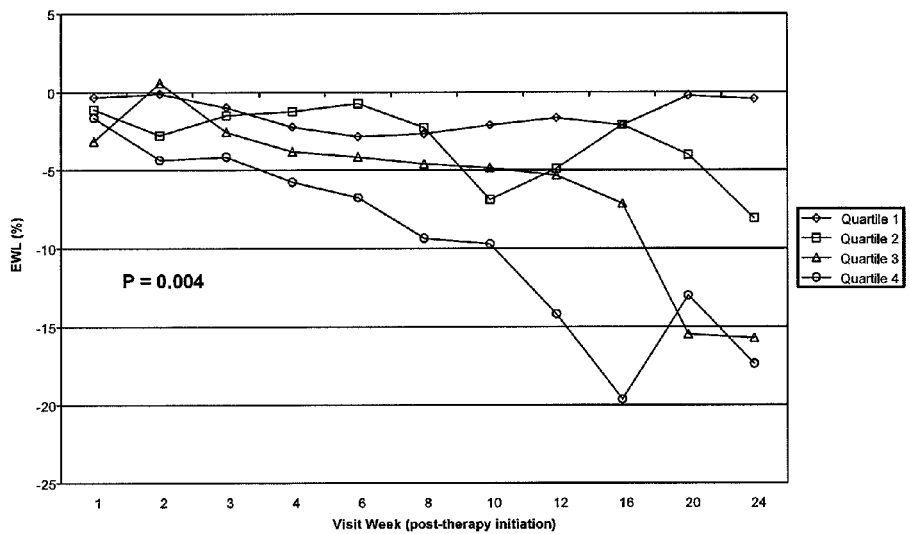
FIG. 11

FIG. 14
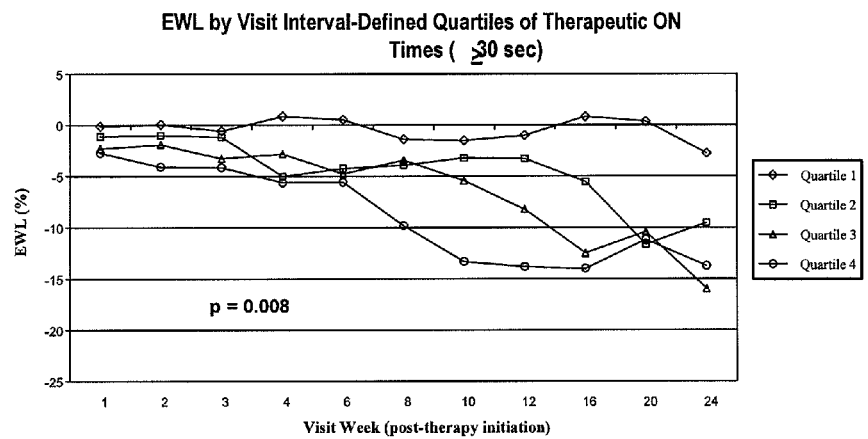
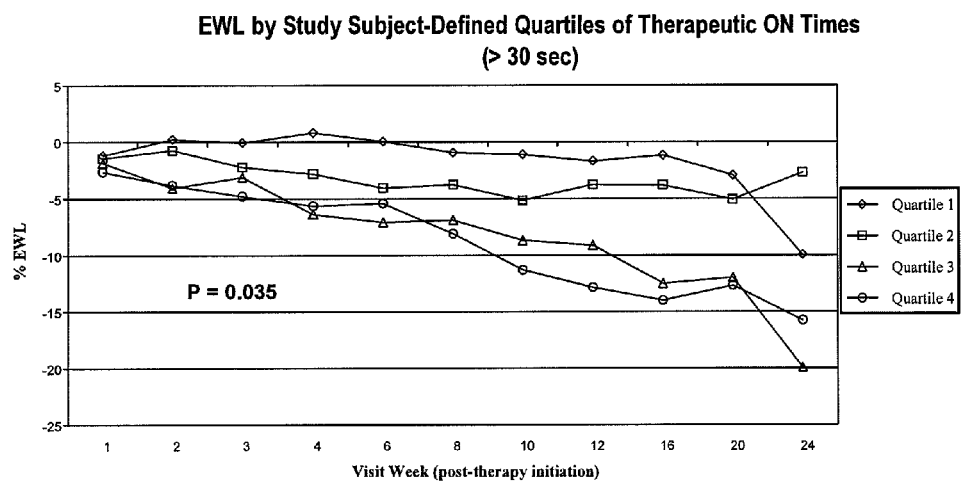
FIG. 15

| Bin | ON times | Parameter Estimate | Standard Error | P-value |
|---|---|---|---|---|
| 1 | 0–30sec | −0.00130 | 0.00028 | <0.0001 |
| 2 | 31–60sec | −0.01095 | 0.00238 | <0.0001 |
| 3 | >1to2 min | −0.01617 | 0.00358 | <0.0001 |
| 4 | >2to3 min | −0.02978 | 0.00608 | <0.0001 |
| 5 | >3to4 min | −0.00327 | 0.00172 | 0.058 |
| 6 | >4to5 min | −0.00451 | 0.00064 | <0.0001 |
| 7 | > 5 min | N/A | N/A | N/A |

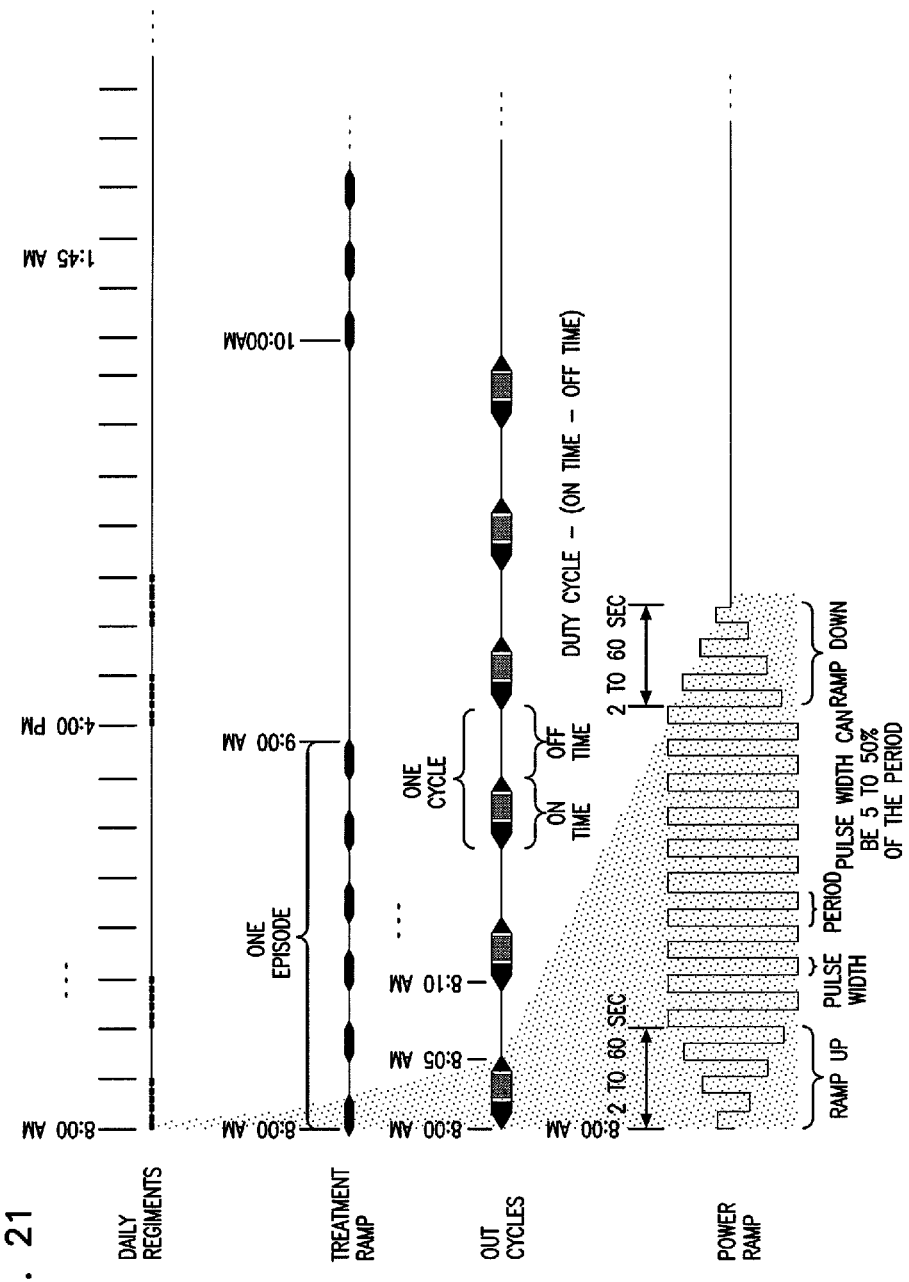

TREATMENT OF EXCESS WEIGHT BY NEURAL DOWNREGULATION IN COMBINATION WITH COMPOSITIONS

CROSS REFERENCE TO RELATED APPLICATIONS

This application claims benefit of Provisional Application No. 61/028,691, filed Feb. 14, 2008, which application is incorporated herein by reference.

BACKGROUND OF THE INVENTION

1. Field of the Invention

This invention pertains to treating subjects having a condition associated with excess weight comprising downregulating neural activity on the vagus nerve and administering a composition that alters the energy balance of the subject.

2. Background

Obesity and other eating disorders are serious health conditions that lead to increased morbidity and mortality. Over the last decade, the prevalence of obesity has increased more than 80%, representing an estimated 43 million adults in 2002. (Mokdad A H, et al, The spread of the obesity epidemic in the United States, 1991-1998. JAMA 1999; (282):1519-22) In terms of mortality, an estimated 280,000 to 325,000 adults in the United States die each year from causes related to obesity. (Allison D B et al, Annual deaths attributable to obesity in the United States. JAMA 1999; 282:1530-8) More importantly, excess weight has been positively correlated with years of life lost. (Fontaine K R et al., Years of life lost due to obesity. JAMA 2003; (289):187-93).

In addition to mortality, substantial morbidity is associated with obesity. For example, in 2000, the total cost of obesity in the United States was estimated to be $117 billion ($61 billion in direct medical costs, $56 billion in indirect costs). (U.S. Department of Health and Human Services. The Surgeon General's call to action to prevent and decrease overweight and obesity. Rockville, Md.: U.S. Department of Health and Human Services, Public Health Service, Office of the Surgeon General; 2001). An estimated 9.1% of annual medical spending in the United States is attributed to overweight and obesity—a figure that rivals medical costs attributable to cigarette smoking.

Treatments for overweight and/or obese patients include both non pharmaceutical and pharmaceutical treatments. Non pharmaceutical treatments include diet, exercise, nerve stimulation, nerve block, and surgical treatments. Pharmaceutical treatments include appetite suppressants, energy expenditure modifying agents, antidepressants, and uptake of nutrient inhibitors. Despite the existence of several treatments, the number of people that are obese or have other eating disorders as well as the costs associated with these conditions continue to rise.

A wide variety of disorders where the treatment includes blocking neural impulses on the vagus nerve have been described. Specific disorders treated include obesity and other eating disorders. Such treatments are described in commonly assigned U.S. Pat. No. 7,167,750 to Knudson et al. issued Jan. 23, 2007 and in the following commonly assigned U.S. patent applications: US 2005/0131485 A1 published Jun. 16, 2005, US 2005/0038484 A1 published Feb. 17, 2005, US 2004/0172088 A1 published Sep. 2, 2004, US 2004/0172085 A1 published Sep. 2, 2004, US 2004/0176812 A1 published Sep. 9, 2004 and US 2004/0172086 A1 published Sep. 2, 2004.

Since 1995, several agents have been available for treatment of obesity and other eating disorders. However, in the case of obesity, the amount of weight lost has been modest even with long term treatment. In addition, several of the agents are known to have serious side effects at the doses that are effective for weight loss. For example, fenfluramine and dexfenfluramine were withdrawn from the market due to a reported association between administration of these drugs and valvular heart disease. Clinical Guidelines of the Identification, Evaluation, and Treatment of Overweight and Obesity in Adults. NIH Publication No. 98-4083, September 1998.

Thus, there remains a need to develop effective treatments for conditions associated with excess weight.

SUMMARY

This disclosure is directed to systems and methods for treating a condition associated with excess weight in a subject comprising: applying an intermittent neural block to the vagus nerve at a blocking site with said neural conduction block selected to down-regulate afferent and/or efferent neural activity on the nerve and with neural activity restoring upon discontinuance of said block; and administering a composition to the subject comprising an effective amount of an agent that alters the energy balance of the subject. Conditions associated with excess weight in a subject include such conditions as obesity, compulsive overeating, bulimia. In some cases, the combination of treatments may provide for a synergistic effect on weight loss and/or a decrease in the amount of an agent that alters energy balance required to be effective, thereby minimizing side effects. In some cases, the methods can be applied to a subject who is overweight and has not yet become obese.

Another aspect of the disclosure provides a system for designing a therapy including a therapy signal and an agent that alters the energy balance of a subject comprising: at least one electrode configured to be implanted within a body of the patient beneath a skin layer and placed at a vagus nerve, the electrode also configured to apply therapy to the vagus nerve upon application of a therapy signal to the electrode; an implantable component for placement in the body of the patient beneath the skin layer, the implantable component being configured to generate the therapy signal and to transmit the therapy signal to the electrode, the implantable component being coupled to an implanted antenna; an external component configured to couple to a first external antenna configured to be placed above the skin layer and adapted to communicate with the implanted antenna across the skin layer through radiofrequency communication, the external component including a plurality of selectable operating modules, each operating module being associated with a different set of operations available for selection by a user; an external programmer configured to communicatively couple to the external component via a second port, the external programmer being configured to provide therapy instructions comprising parameters for each therapy cycle to the external component, wherein the external component is configured to send the therapy instructions to the implantable component via the external antenna and the implanted antenna, and the parameters comprise a therapy signal selected to downregulate activity on the vagus nerve with an on time period and off time period, the off time period selected to allow partial recovery of nerve function; and the external programmer being configured to allow the user to select an agent that alters energy balance in the patient based on the health profile of the patient and the side effects of the agent.

Another aspect of the disclosure provides methods for selecting a therapy cycle for an implantable device and for selecting an agent that alters energy balance in a subject. In one embodiment, the method comprises selecting parameters of a therapy cycle to be applied to a vagus nerve to provide weight loss to the subject, wherein the parameters comprise an electrical signal having a frequency of 300 Hz or greater, having an on time of at least 30 seconds, and having an off time that allows partial recovery of the nerve; communicating the selected parameters to the implantable device and delivering at least 10 therapy cycles during a treatment period, and selecting an agent and a dosage of agent that alters the energy balance of the subject based on the health profile of the subject and the side effects of the agent using an external programmer.

BRIEF DESCRIPTION OF THE DRAWINGS

FIG. 10 is a graph illustrating percent excess weight loss over time experienced by patients grouped into visit interval-defined quartiles based on frequency of occurrence of ON times with durations less than 30 seconds;

FIG. 11 is a graph similar to that of FIG. 10 for patients grouped into visit interval-defined quartiles based on frequency of occurrence of ON times with durations between 30 and 180 seconds;

FIG. 14 is a graph similar to that of FIG. 10 for patients grouped into visit interval-defined quartiles based on frequency of occurrence of ON times with durations greater than or equal to 30 seconds;

FIG. 15 is a graph similar to that of FIG. 14 for patients grouped into subject-defined quartiles based on frequency of occurrence of ON times with durations greater than or equal to 30 seconds;

FIG. 21 is a graph illustrating a typical duty cycle.

DETAILED DESCRIPTION

The following commonly assigned patent and U.S. patent applications are incorporated herein by reference: U.S. Pat. No. 7,167,750 to Knudson et al. issued Jan. 23, 2007; US 2005/0131485 A1 published Jun. 16, 2005, US 2005/0038484 A1 published Feb. 17, 2005, US 2004/0172088 A1 published Sep. 2, 2004, US 2004/0172085 A1 published Sep. 2, 2004, US 2004/0176812 A1 published Sep. 9, 2004 and US 2004/0172086 A1 published Sep. 2, 2004. Also incorporated herein by reference is International patent application Publication No. WO 2006/023498 A1 published Mar. 2, 2006.

A. Description of Vagal Innervation of the Alimentary Tract

Figure 1:
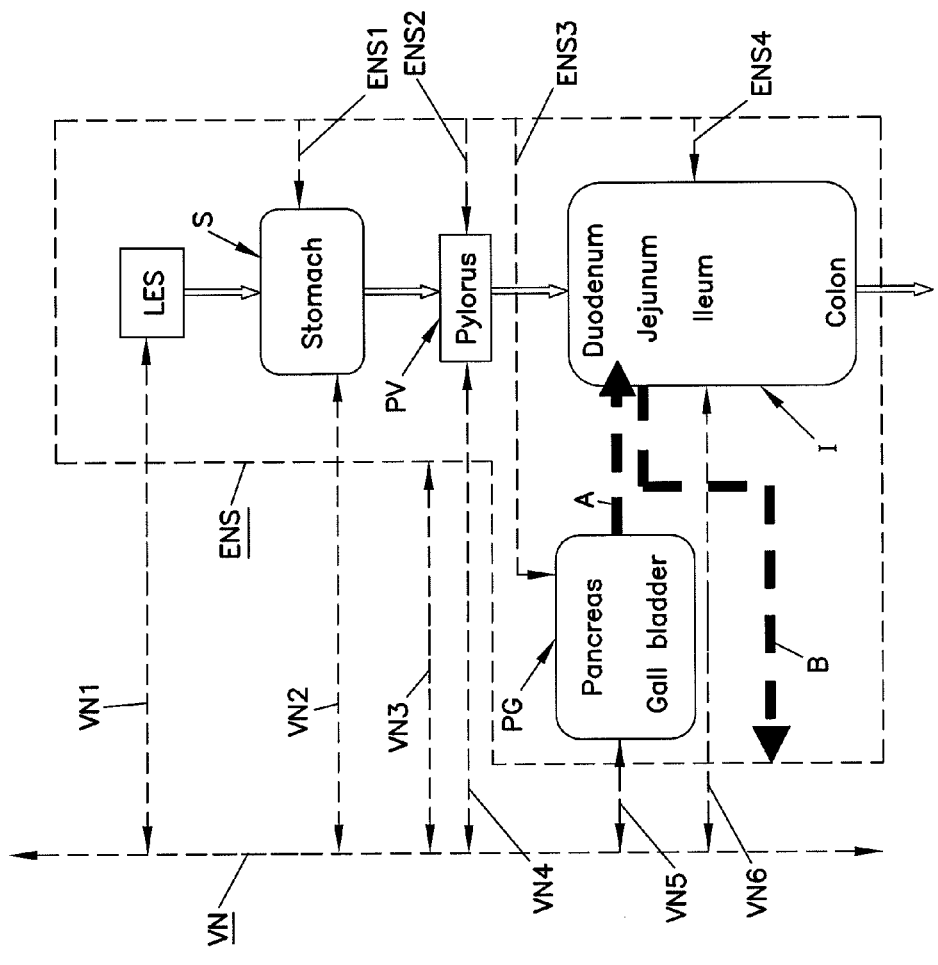
FIG. 1 is a schematic illustration of an alimentary tract (GI tract plus non-GI organs such as the pancreas and liver) and its relation to vagal and enteric innervation.

FIG. 1 is a schematic illustration of an alimentary tract (GI tract plus non-GI organs such as the pancreas and gall bladder, collectively labeled PG) and its relation to vagal and enteric innervation. The lower esophageal sphincter (LES) acts as a gate to pass food into the stomach S and, assuming adequate function of all components, prevent reflux. The pylorus PV controls passage of chyme from the stomach S into the intestines I (collectively shown in the figures and including the large intestine or colon and the small intestine including the duodenum, jejunum and ileum). The biochemistry of the contents of the intestines I is influenced by the pancreas P and gall bladder PG which discharge into the duodenum. This discharge is illustrated by dotted arrow A.

Figure 2:
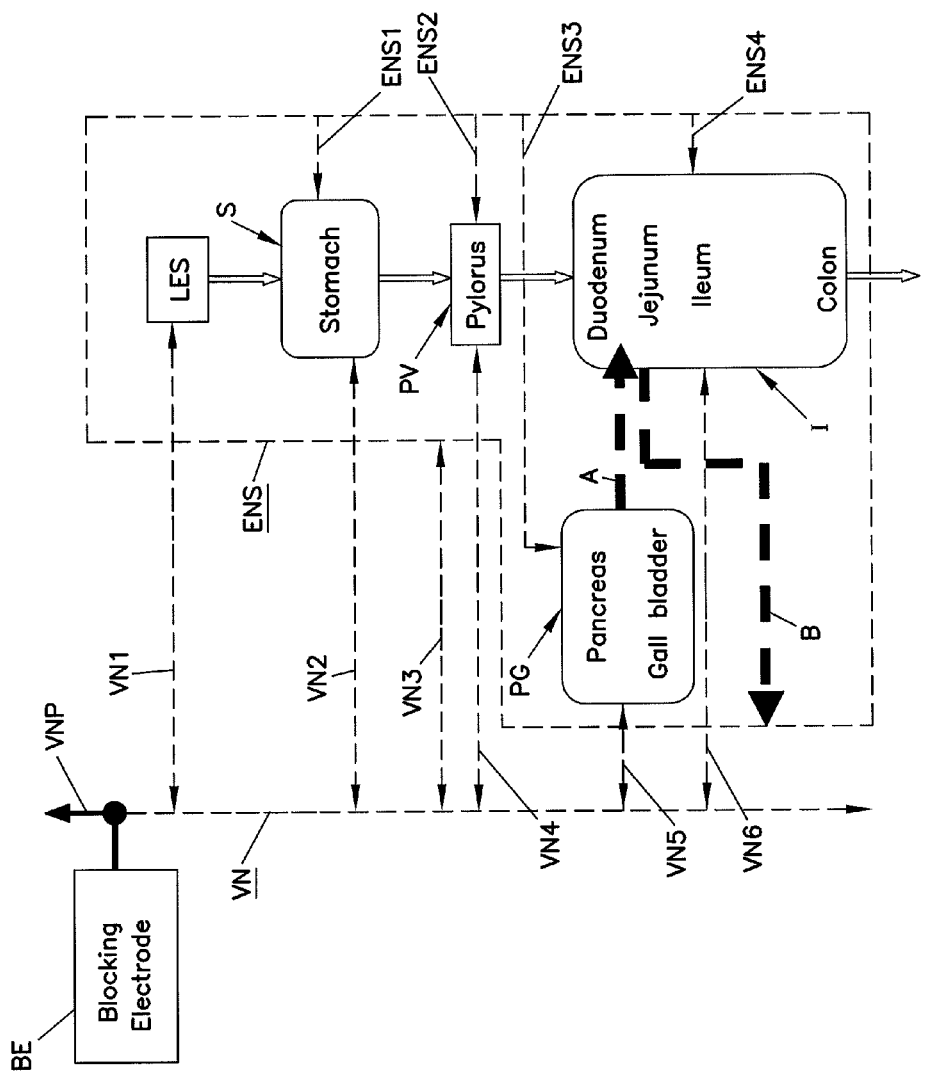
FIG. 2 is the view of FIG. 1 showing the application of a nerve conduction block electrode to the alimentary tract.

The vagus nerve VN transmits signals to the stomach S, pylorus PV, pancreas and gall bladder PG directly. Originating in the brain, there is a common vagus nerve VN in the region of the diaphragm (not shown). In the region of the diaphragm, the vagus VN separates into anterior and posterior components with both acting to innervate the GI tract. In FIGS. 1, and 2, the anterior and posterior vagus nerves are not shown separately. Instead, the vagus nerve VN is shown schematically to include both anterior and posterior nerves. The vagus nerve VN contains both afferent and efferent components sending signals to and away from, respectively, its innervated organs.

In addition to influence from the vagus nerve VN, the GI and alimentary tracts are greatly influenced by the enteric nervous system ENS. The enteric nervous system ENS is an interconnected network of nerves, receptors and actuators throughout the GI tract and pancreas and gall bladder PG. There are many millions of nerve endings of the enteric nervous system ENS in the tissues of the GI organs. For ease of illustration, the enteric nervous system ENS is illustrated as a line enveloping the organs innervated by the enteric nervous system ENS. The vagus nerve VN innervates, at least in part, the enteric nervous system ENS (schematically illustrated by vagal trunk VN3 which represents many vagus-ENS innervation throughout the gut). Also, receptors in the intestines I connect to the enteric nervous system ENS. Arrow B in the figures illustrates the influence of duodenal contents on the enteric nervous system ENS as a feedback to the secretion function of the pancreas, liver and gall bladder. Specifically, receptors in the intestine I respond to the biochemistry of the intestine contents (which are chemically modulated by the pancreao-biliary output of Arrow A). This biochemistry includes pH and osmolality.

In FIGS. 1 and 2, vagal trunks VN1, VN2, VN4 and VN6 illustrate schematically the direct vagal innervation of the GI organs of the LES, stomach S, pylorus PV and intestines I. Trunk VN3 illustrates direct communication between the vagus VN and the ENS. Trunk VN5 illustrates direct vagal innervation of the pancreas and gall bladder. Enteric nerves ENS1-ENS4 represent the multitude of enteric nerves in the stomach S, pylorus PV, pancreas and gall bladder PG and intestines I.

While communicating with the vagus nerve VN, the enteric nervous system ENS can act independently of the vagus and the central nervous system. For example, in patients with a severed vagus nerve (vagotomy—a historical procedure for treating ulcers), the enteric nervous system can operate the gut. Most enteric nerve cells are not directly innervated by the vagus. Gershon, "The Second Brain", Harper Collins Publishers, Inc, New York, N.Y. p. 19 (1998).

B. Therapy Delivery Equipment

The disclosure provides systems for treating a condition associated with excess weight comprising an impulse generator that provides signals to modulate neural activity on the vagus nerve.

In an embodiment, a system (schematically shown in FIG. 3) for designing a therapy or for treating such conditions including obesity or other eating disorders includes an impulse generator 104, an external mobile charger 101, and two electrical lead assemblies 106, 106a, each comprising an electrode.

The impulse generator 104 is adapted for implantation within a patient to be treated. The impulse generator 104 is implanted just beneath a skin layer 103.

In some embodiments, the lead assemblies 106, 106a are electrically connected to the circuitry of the impulse generator 104 by conductors 114, 114a. Industry standard connectors 122, 122a are provided for connecting the lead assemblies 106, 106a to the conductors 114, 114a. As a result, leads 106, 106a and the impulse generator 104 may be separately implanted. Also, following implantation, lead 106, 106a may be left in place while the originally placed impulse generator 104 is replaced by a different impulse generator.

The leads 106, 106a have distal electrodes 212, 212a which are individually placed on the anterior and posterior vagal nerves AVN, PVN, respectively, of a patient, for example, just below the patient's diaphragm. It will be appreciated that the description of two electrodes directly placed on a nerve is a description of a preferred embodiment. Fewer or more electrodes can be placed on or near fewer or more nerves. In some embodiments, the electrodes are cuff electrodes.

In an embodiment, the external component comprises a mobile charger 101 that includes circuitry for communicating with the implanted impulse generator 104. In some embodiments, the communication is a two-way radiofrequency (RF) signal path across the skin 103 as indicated by arrows A. In embodiments, the external component comprises a plurality of selectable operating modules, each operating module being associated with a different set of operations available for selection by a user.

Figure 3:
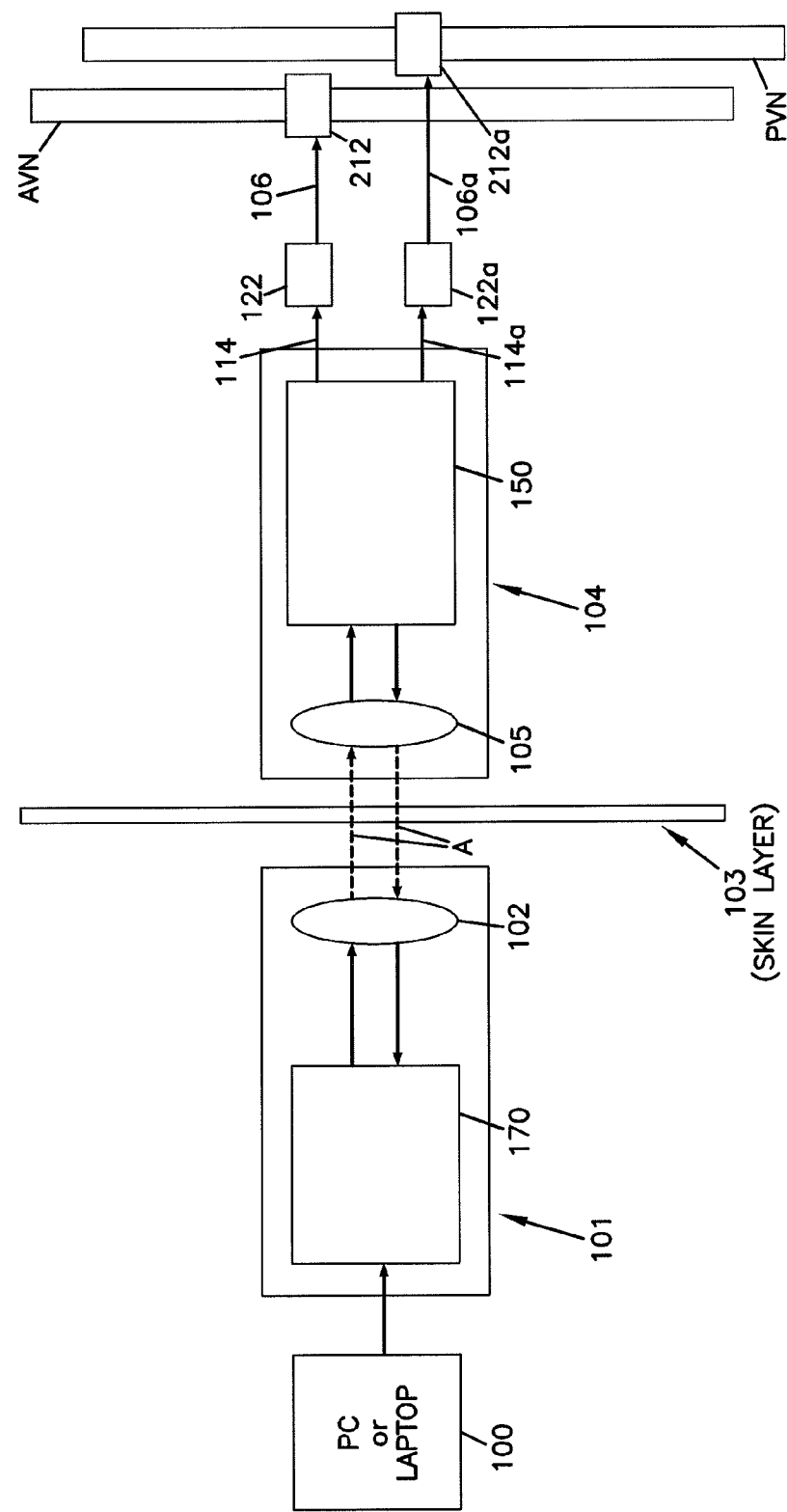
FIG. 3. is a schematic representation of an implantable system configuration for a gastro-intestinal treatment involving applying an electrical signal to a vagus nerve.

Referring to FIG. 3, an external programmer such as a computer (such as a personal computer) 100 can be connected to the external component 101. With such a connection, a physician can use the computer 100 to program therapies into the impulse generator 104 as will be described. In embodiments, the external programmer is configured to provide therapy instructions comprising parameters for each therapy cycle to the external component, and the parameters comprise a therapy signal selected to downregulate activity on the vagus nerve with an on time period and off time period, the off time period selected to allow partial recovery of nerve function, and the external programmer is configured to allow the user to select an agent that alters energy balance in the patient based on the health profile of the patient and the side effects of the agent.

In embodiments, the implantable component is configured to deliver a therapy cycle comprising an electrical signal having a frequency of at least 300 Hz, an on time of at least 30 seconds, and an off time that allows for partial recovery of the nerve function. The implantable component may be configured to generate therapy signals for a treatment period. In some cases, the treatment period is at least 8 hours. In some embodiments, the frequency of the electrical signal ranges from 300 to 10,000 Hz, about 500 to 8000 Hz, or about 1000 to about 5000 Hz. In some embodiments, the frequency of the electrical signal is about 2500 to 5000 Hz. An on time for the signal of a therapy cycle can range from 30 seconds to 3 minutes, 30 seconds to 2 minutes, or from 30 seconds to 1 minute. The on time can optionally include a ramp up and a ramp down time of about 2 to 60 seconds. The off times of the electrical signal in the therapy cycle are selected to allow at least a partial recovery of nerve function. The off times can be selected from 1 minute to about 20 minutes, 1 minute to 10 minutes, or 1 minute to 5 minutes.

In other embodiments, the external programmer is configured to provide therapy instructions comprising parameters for the therapy cycle to the external component, wherein the parameters of the therapy cycle comprise an electrical signal with a frequency of at least 300 Hz with an on time of at least 30 seconds and an off time that allows partial recovery of nerve function. The parameters can vary as described above. The external programmer can be configured to provide therapy instructions to the external component comprising multiple therapy cycles in a treatment period. In embodiments, a treatment period is from 1 hour to 24 hours, 1 hour to about 12 hours, 1 hour to 8 hours, or 1 hour to 4 hours. In embodiments, the external programmer is configured to provide therapy instructions that include multiple therapy cycles per treatment period. In some embodiments, at least ten therapy cycles are delivered per treatment period. In other embodiments, at least 10 to 600, 20 to 250, or 50 to 100 therapy cycles are delivered in a treatment period.

In embodiments, the external programmer is configured to obtain patient data, wherein the patient data comprises data obtained from the implantable component and patient data concerning the health profile of the patient. A health profile may include the presence or absence of conditions in a subject selected from the group consisting of diabetes, hypertension, cardiac condition, liver disorder, a renal disorder and combinations thereof. A health profile may also include age of the patient, the presence of other implantable devices, and medications taken by the patient.

In some embodiments, the external programmer is configured to obtain data about dosages and side effects of agents that alter energy balance. The agents that alter energy balance comprise agents that enhance the sensation of satiety, agents that decrease appetite, agents that block the absorption of fat or other nutrients, agents that inhibit enzymes that digest fat, agents that are thermogenic, or combinations thereof. Examples of such agents are described herein and include ghrelin, leptin, CNTF, amylin, PYY, CKK, GLP-1 and analogues or antagonists thereof. Other agents include sibutramine, fenfluramine, phenteramine, fluoxetine, and bupropion. Side effects associated with a particular agent may include cardiac arrhythmias, cardiac valve disease, seizures, increased blood pressure, depression, anxiety, diarrhea, increased fat in the stool and combinations thereof.

The circuitry 170 of the external component 101 can be connected to a first coil 102. The coil 102 communicates with a similar coil 105 implanted within the patient and connected to the circuitry 150 of the impulse generator 104. The external component is configured to send the therapy instructions to the implantable impulse generator via the external antenna and the implanted antenna, Communication between the external component 101 and the impulse generator 104 includes transmission of pacing parameters and other signals as will be described.

In embodiments, the selectable operating modules comprise: an operating room module that is selectable when the external component is coupled to the first external antenna, the operating room module being associated with at least a testing operation to test appropriate positioning of the implantable component within the body; a therapy delivery module that is selectable when the external component is coupled to a second external antenna, the therapy delivery module being associated with therapy signal generation; and a diagnostic module that is selectable when the external component is coupled to an external programmer, the programming module being configured to transfer a therapy schedule from the external programmer to the implantable component.

Having been programmed by signals from the external component 101, the impulse generator 104 generates blocking signals or downregulating signals to the leads 106, 106*a*. As will be described, the external component 101 may have additional functions in that it may provide for periodic recharging of batteries within the impulse generator 104, and also allow record keeping and monitoring.

While an implantable (rechargeable) power source for the impulse generator 104 is preferred, an alternative design could utilize an external source of power, the power being transmitted to an implanted module via the RF link (i.e., between coils 102, 105). In this alternative configuration, while powered externally, the source of the specific blocking signals could originate either in the external power source unit, or in the implanted module.

Figure 5:
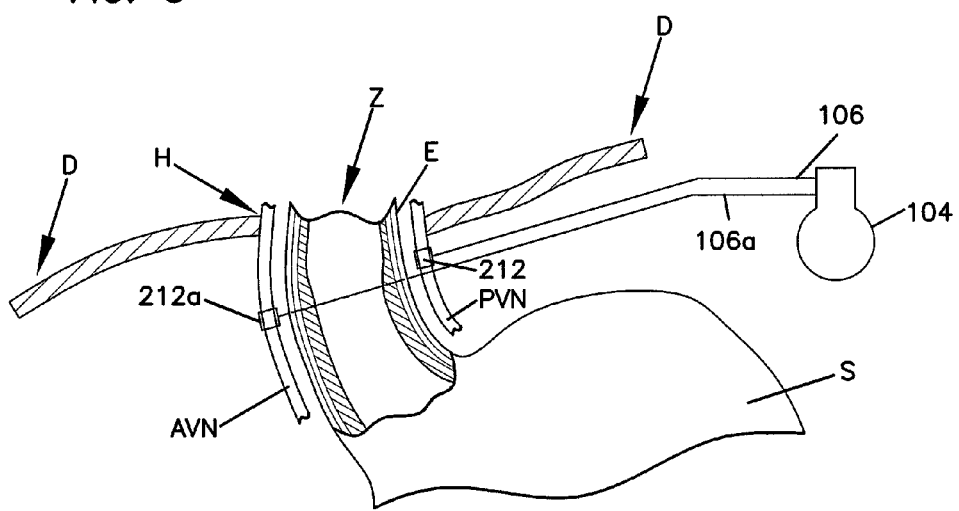
FIG. 5 illustrates an impulse generator, leads and placement of anterior and posterior electrodes on the vagus nerve.

Another embodiment of a system useful in treating a condition associated with excess weight as described herein is shown in FIG. 5.

Figure 4:
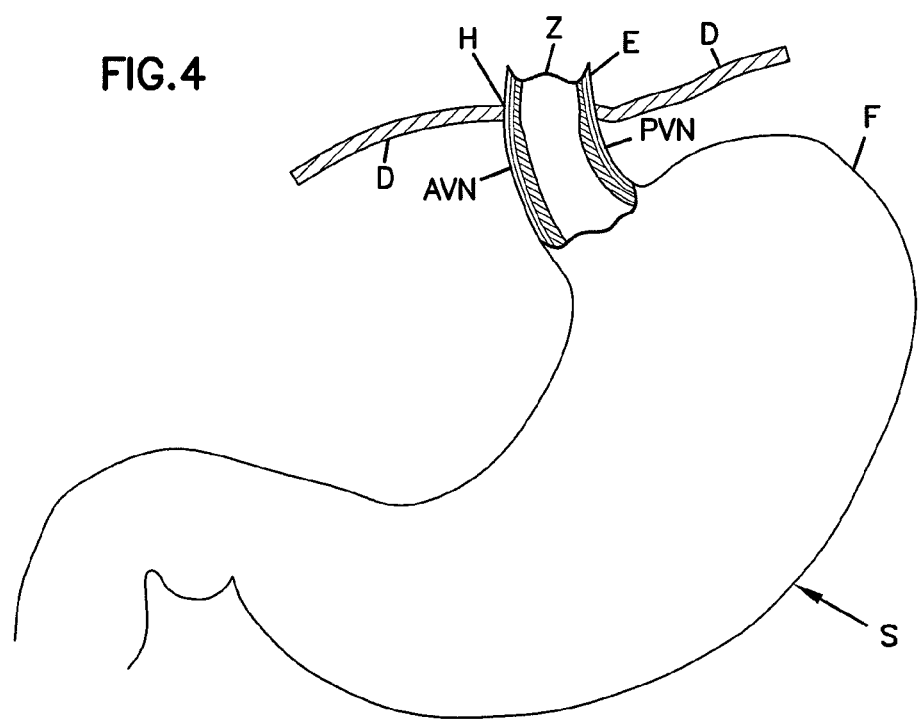
FIG. 4 is a schematic representation of a patient's stomach shown partially in section and illustrating a representative placement of anterior and posterior vagus nerves with respect to the anatomy of the stomach and diaphragm.

With reference to FIG. 4, a stomach S is shown schematically for the purpose of facilitating an understanding of applying a vagal nerve modulating signal. In FIG. 4, the stomach S is shown with a collapsed fundus F which is deflated due to fasting. In practice, the fundus F can be reduced in size and volume (as shown in FIG. 4) or expanded. The esophagus E passes through the diaphragm D at an opening or hiatus H. In the region where the esophagus E passes through the diaphragm D, trunks of the vagal nerve (illustrated as the anterior vagus nerve AVN and posterior vagus nerve PVN) are disposed on opposite sides of the esophagus E. It will be appreciated that the precise location of the anterior and posterior vagus nerves AVN, PVN relative to one another and to the esophagus E are subject to a wide degree of variation within a patient population. However, for most patients, the anterior and posterior vagus nerves AVN, PVN are in close proximity to the esophagus E at the hiatus H where the esophagus E passes through the diaphragm D.

The anterior and posterior vagus nerves AVN, PVN divide into a plurality of trunks that innervate the stomach directly and via the enteric nervous system and may include portions of the nerves which may proceed to other organs such as the pancreas, gallbladder and intestines. Commonly, the anterior and posterior vagus nerves AVN, PVN are still in close proximity to the esophagus E and stomach (and not yet extensively branched out) at the region of the junction of the esophagus E and stomach S.

In the region of the hiatus H, there is a transition from esophageal tissue to gastric tissue. This region is referred to as the Z-line (labeled "Z" in the Figures). Above the Z-line, the tissue of the esophagus is thin and fragile. Below the Z-line, the tissue of the esophagus E and stomach S are substantially thickened and more vascular. Within a patient population, the Z-line is in the general region of the lower esophageal sphincter. This location may be slightly above, slightly below or at the location of the hiatus H.

With reference to FIG. 5, electrodes 212, 212*a* are shown placed near the esophagus E or proximal portion of the stomach below the diaphragm D and on the anterior and posterior vagus nerves AVN, PVN. In a preferred embodiment, the nerves AVN, PVN are indirectly stimulated by passing electrical signals through the tissue surrounding the nerves. In some embodiments, the electrodes are bipolar pairs (ie. alternating anode and cathode electrodes). In some embodiments, a plurality of electrodes may be placed overlying the anterior and/or posterior vagus nerves AVN, PVN. As a result, energizing the plurality of electrodes will result in application of a signal to the anterior and posterior vagus nerves AVN, PVN and/or their branches. In some therapeutic applications, some of the electrodes may be connected to a blocking electrical signal source (with a blocking frequency and other parameters as described below). Of course, only a single array of electrodes could be used with all electrodes connected to a blocking or a downregulating signal.

The electrical connection of the electrodes to an impulse generator may be as previously described by having a leads (eg. 106,106*a*) connecting the electrodes directly to an implantable impulse generator (eg. 104). Alternatively, and as previously described, electrodes may be connected to an implanted antenna for receiving a signal to energize the electrodes.

Impulse Generator

The impulse generator generates electrical signals in the form of electrical impulses according to a programmed regimen. In embodiments, a blocking signal is applied as described herein.

The impulse generator utilizes a microprocessor and other standard electrical and electronic components, and communicates with an external programmer and/or monitor by asynchronous serial communication for controlling or indicating states of the device. Passwords, handshakes and parity checks are employed for data integrity. The impulse generator also includes means for conserving energy, which is important in any battery operated device and especially so where the device is implanted for medical treatment of a disorder, and means for providing various safety functions such as preventing accidental reset of the device.

Features may be incorporated into the impulse generator for purposes of the safety and comfort of the patient. In some embodiments, the patient's comfort would be enhanced by ramping the application of the signal up during the first two seconds. The device may also have a clamping circuit to limit the maximum voltage (14 volts for example) deliverable to the vagus nerve, to prevent nerve damage. An additional safety function may be provided by implementing the device to cease signal application in response to manual deactivation through techniques and means similar to those described above for manual activation. In this way, the patient may interrupt the signal application if for any reason it suddenly becomes intolerable.

The intermittent aspect of the blocking resides in applying the signal according to a prescribed duty cycle. The pulse signal is programmed to have a predetermined on-time in which a train or series of electrical pulses of preset parameters is applied to the vagus branches, followed by a predetermined off-time. Nevertheless, continuous application of the electrical pulse signal may also be effective.

Impulse generators, one supplying the right vagus and the other the left vagus to provide the bilateral blocking or down-regulation may be used. Use of implanted impulse generator for performing methods as described herein is preferred, but treatment may conceivably be administered using external equipment on an outpatient basis, albeit only somewhat less confining than complete hospitalization. Implantation of one or more impulse generators, of course, allows the patient to be completely ambulatory, so that normal daily routine activities including on the job performance is unaffected.

Signals can be applied at a portion of the nervous system remote from the vagus nerve such as at or near the stomach wall, for indirect regulation of the vagus nerve in the vicinity of the sub-diaphragmatic location. Here, at least one impulse generator is implanted together with one or more electrodes subsequently operatively coupled to the impulse generator via leads for generating and applying the electrical signal internally to a portion of the patient's nervous system to provide indirect blocking or down regulation of the vagus nerve in the vicinity of the desired location. Alternatively, the electrical signal may be applied non-invasively to a portion of the patient's nervous system for indirect application of the vagus nerve at a sub-diaphragmatic location.

The impulse generator may be programmed with an external programmer such as a programming wand and a personal computer using suitable programming software developed according to the programming needs and signal parameters which have been described herein. The intention, of course, is to permit noninvasive communication with the electronics package after the latter is implanted, for both monitoring and programming functions. Beyond the essential functions, the programming software should be structured to provide straightforward, menu-driven operation, HELP functions, prompts, and messages to facilitate simple and rapid programming while keeping the user fully informed of everything occurring at each step of a sequence. Programming capabilities should include capability to modify the electronics package's adjustable parameters, to test device diagnostics, and to store and retrieve telemetered data. It is desirable that when the implanted unit is interrogated, the present state of the adjustable parameters is displayed on the PC monitor so that the programmer may then conveniently change any or all of those parameters at the same time; and, if a particular parameter is selected for change, all permissible values for that parameter are displayed so that the programmer may select an appropriate desired value for entry into the impulse generator.

Other desirable features of appropriate software and related electronics would include the capability to store and retrieve historical data, including patient code, device serial number, number of hours of battery operation, number of hours of output, and number of magnetic activations (indicating patient intercession) for display on a screen with information showing date and time of the last one or more activations.

In embodiments, the external programmer is configured to obtain and store patient data concerning the health profile of the patient. A health profile may include the presence or absence of conditions in a subject selected from the group consisting of diabetes, hypertension, cardiac condition, liver disorder, a renal disorder and combinations thereof. A health profile may also include age of the patient, the presence of other implantable devices, and medications taken by the patient.

In some embodiments, the external programmer is configured to obtain and store data about dosages and side effects of agents that alter energy balance. The agents that alter energy balance comprise agents that enhance the sensation of satiety, agents that decrease appetite, agents that block the absorption of fat or other nutrients, agents that inhibit enzymes that digest fat, agents that are thermogenic, or combinations thereof. Examples of such agents are described herein and include ghrelin, leptin, CNTF, amylin, PYY, CKK, GLP-1 and analogues or antagonists thereof. Other agents include sibutramine, fenfluramine, phenteramine, fluoxetine, and bupropion. Side effects associated with a particular agent may include cardiac arrhythmias, cardiac valve disease, seizures, increased blood pressure, depression, anxiety, diarrhea, increased fat in the stool and combinations thereof.

Diagnostics testing should be implemented to verify proper operation of the device, and to indicate the existence of problems such as with communication, the battery, or the lead/electrode impedance. A low battery reading, for example, would be indicative of imminent end of life of the battery and need for implantation of a new device. However, battery life should considerably exceed that of other implantable medical devices, such as cardiac pacemakers, because of the relatively less frequent need for activation of the pulse generator of the present invention. In any event, the nerve electrodes are capable of indefinite use absent indication of a problem with them observed on the diagnostics testing.

The device may utilize circadian or other programming as well, so that activation occurs automatically at normal mealtimes for this patient. This may be in addition to the provision for the manual, periodic between meal, and sensing-triggered activation as described above herein.

C. Methods

The disclosure provides a method for manufacturing a system comprising: providing at least one electrode configured to be implanted within a body of the patient beneath a skin layer and placed at a vagus nerve, the electrode also configured to apply therapy to the vagus nerve upon application of a therapy signal to the electrode; providing an implantable component for placement in the body of the patient beneath the skin layer, the implantable component being coupled to an implanted antenna and the electrode, and configuring the implantable component to generate the therapy signal and to transmit the therapy signal to the electrode; providing an external component to be placed above the skin layer and adapted to communicate with the implanted antenna across the skin layer through radiofrequency communication, the external component including a plurality of selectable operating modules, each operating module being associated with a different set of operations available for selection by a user and configuring the external component to couple to a first external antenna and to send the therapy instructions to the implantable component via the first external antenna and the implanted antenna; providing an external programmer and configuring the external programmer to a) communicatively couple to the external component via a second port, b) to provide therapy instructions comprising parameters for each therapy cycle to the external component, wherein the parameters comprise a therapy signal selected to downregulate activity on the vagus nerve with an on time period and off time period, the off time period selected to allow partial recovery of nerve function; and c) to allow the user to select an agent that alters energy balance in the patient based on the health profile of the patient and the side effects of the agent.

In other embodiments, the disclosure provides a method of selecting parameters for a therapy cycle for an implantable device and of selecting an agent, wherein the therapy cycle and the agent alter energy balance in a subject comprising: selecting parameters of a therapy cycle to be applied to a vagus nerve to provide weight loss to the subject, wherein the parameters comprise an electrical signal having a frequency of 300 Hz or greater, having an on time of at least 30 seconds, and having an off time that allows partial recovery of the nerve; communicating the selected parameters to an implantable device such as provided in the system of claim 1 and delivering at least 10 therapy cycles during a treatment period, and selecting an agent and a dosage of agent that alters the energy balance of the subject based on the health profile of the subject and the side effects of the agent using an external programmer such as provided in the system of claim 1.

The disclosure provides methods of treating a condition associated with excess weight in a subject by modulating neural activity of the vagus nerve in combination with administration of an agent that alters the energy balance in the subject. In some embodiments, a method comprises: applying an intermittent neural block to the vagus nerve at a blocking site with said neural conduction block selected to down-regulate neural activity on the nerve and with neural activity restoring upon discontinuance of said block; and administering a composition to the subject comprising an effective amount of an agent that alters the energy balance of the subject. In some embodiments, the neural block is applied to the nerve by implanting a device as described herein. Conditions associated with excess weight include, without limitation, obesity, compulsive eating, and bulimia.

Down Regulating Signal Application

In embodiments of the methods described herein a signal is applied to the vagus nerve at a site with said signal selected to down-regulate neural activity on the nerve and with neural activity restoring upon discontinuance of said signal. Methods and systems for applying such a signal are been described U.S. Pat. No. 7,167,750; US2005/0038484 which is incorporated by reference.

The signal is selected to down regulate neural activity and allow for restoration of the neural activity upon discontinuance of the signal. An impulse generator, as described above, is employed to regulate the application of the signal in order alter the characteristic of the signal to provide a reversible intermittent signal. The characteristics of the signal include frequency of the signal, location of the signal, and the administration cycle of the signal. Signal characteristics are selected to enhance a sensation of satiety, to modulate intestinal motility and rate of digestion, and/or partial restoration of the nerve following discontinuance of the signal. Signal characteristics selected that provide for down regulation of neural activity and restoration of neural activity upon discontinuance of the signal include signal frequency, electrode placement and signal type and timing.

In some embodiments, electrodes applied to both anterior and posterior vagal trunks are energized with a blocking or down regulating signal. The signal is applied for a limited time (e.g., 5 minutes). The speed of vagal activity recovery varies from subject to subject. However, 20 minutes is a reasonable example of the time needed to recover to baseline. After recovery, application of a blocking signal again down-regulates vagal activity which can then recover after cessation of the signal. Renewed application of the signal can be applied before full recovery. For example, after a limited time period (e.g., 10 minutes) blocking can be renewed resulting in average vagal activity not exceeding a level significantly reduced when compared to baseline.

In embodiments, the implantable component is configured to deliver a therapy cycle comprising an electrical signal having a frequency of at least 300 Hz, an on time of at least 30 seconds, and an off time that allows for partial recovery of the nerve function. The implantable component may be configured to generate therapy signals for a treatment period. In some cases, the treatment period is at least 8 hours. In some embodiments, the frequency of the electrical signal ranges from 300 to 10,000 Hz, about 500 to 8000 Hz, or about 1000 to about 5000 Hz. In some embodiments, the frequency of the electrical signal is about 2500 to 5000 Hz. An on time for the signal of a therapy cycle can range from 30 seconds to 3 minutes, 30 seconds to 2 minutes, or from 30 seconds to 1 minute. The on time can optionally include a ramp up and a ramp down time of about 2 to 60 seconds. The off times of the electrical signal in the therapy cycle are selected to allow at least a partial recovery of nerve function. The off times can be selected from 1 minute to about 20 minutes, 1 minute to 10 minutes, or 1 minute to 5 minutes.

In other embodiments, the external programmer is configured to provide therapy instructions comprising parameters for the therapy cycle to the external component, wherein the parameters of the therapy cycle comprise an electrical signal with a frequency of at least 300 Hz with an on time of at least 30 seconds and an off time that allows partial recovery of nerve function. The parameters can vary as described above. The external programmer can be configured to provide therapy instructions to the external component comprising multiple therapy cycles in a treatment period. In embodiments, a treatment period is from 1 hour to 24 hours, 1 hour to about 12 hours, 1 hour to 8 hours, or 1 hour to 4 hours. In embodiments, the external programmer is configured to provide therapy instructions that include multiple therapy cycles per treatment period. In some embodiments, at least ten therapy cycles are delivered per treatment period. In other embodiments, 10 to 600, 20 to 250, or 50 to 100 cycles are delivered in a treatment period.

Figure 6:
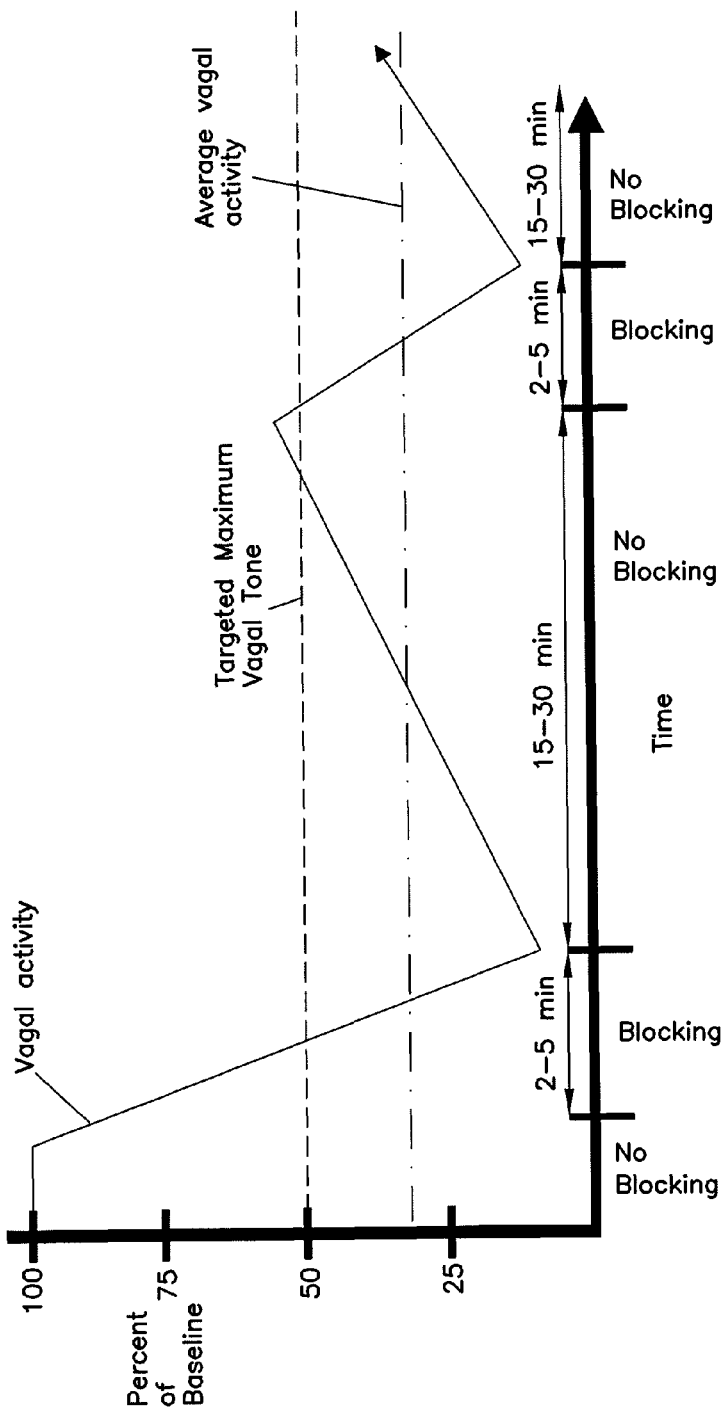
FIG. 6 shows recovery of the vagal nerve after application of blocking signal.

Recognition of recovery of vagal activity (and recognition of the significant variability between subjects) permits a treatment therapy and apparatus with enhanced control and enhanced treatment options. FIG. 6 illustrates vagal activity over time in response to application of a blocking signal as described above and further illustrates recovery of vagal activity following cessation of the blocking signal. It will be appreciated that the graph of FIG. 6 is illustrative only. It is expected there will be significant patient-to-patient variability. For example, some patients' responses to a blocking signal may not be as dramatic as illustrated. Others may experience recovery slopes steeper or shallower than illustrated. Also, vagal activity in some subjects may remain flat at a reduced level before increasing toward baseline activity. However, based on the afore-mentioned animal experiments, FIG. 6 is believed to be a fair presentation of a physiologic response to blocking.

In FIG. 6, vagal activity is illustrated as a percent of baseline (i.e., vagal activity without the treatment of the present invention). Vagal activity can be measured in any number of ways. For example, quantities of pancreatic exocrine secretion produced per unit time are an indirect measurement of such activity. Also, activity can be measured directly by monitoring electrodes on or near the vagus. Such activity can also be ascertained qualitatively (e.g., by a patient's sensation of bloated feelings or normalcy of gastrointestinal motility).

In FIG. 6, the vertical axis is a hypothetical patient's vagal activity as a percent of the patient's baseline activity (which varies from patient to patient). The horizontal axis represents the passage of time and presents illustrative intervals when the patient is either receiving a blocking signal as described or the blocking signal is turned off (labeled "No Blocking"). As shown in FIG. 6, during a short period of receiving the blocking signal, the vagal activity drops dramatically (in the example shown, to about 10% of baseline activity). After cessation of the blocking signal, the vagal activity begins to rise toward baseline (the slope of the rise will vary from patient to patient). The vagal activity can be permitted to return to baseline or, as illustrated in FIG. 6, the blocking signal can be re-instituted when the vagal activity is still reduced. In FIG. 6, the blocking signal begins when the vagal activity increases to about 50% of baseline. As a consequence, the average vagal activity is reduced to about 30% of the baseline activity. It will be appreciated that by varying the blocking time duration and the "no blocking" time duration, the average vagal activity can be greatly varied.

The block may be intermittent or continuous. The preferred nerve conduction block is an electronic block created by a signal at the vagus by an electrode controlled by the implantable impulse generator (such as impulse generator 104). The nerve conduction block can be any reversible block. For example, ultrasound, cryogenics (either chemically or electronically induced) or drug blocks can be used. An electronic cryogenic block may be a Peltier solid-state device which cools in response to a current and may be electrically controlled to regulate cooling. Drug blocks may include a pump-controlled subcutaneous drug delivery.

With such an electrode conduction block, the block parameters (signal type and timing) can be altered by impulse regulator and can be coordinated with the pacing signals to block only during pacing. A representative blocking signal is a 500 Hz signal with other parameters (e.g., timing and current) matched to be the same as the pacing signal. While an alternating current blocking signal is described, a direct current (e.g.,—70 mV DC) could be used.

The foregoing specific examples of blocking signals are representative only. Other examples and ranges of blocking signals are described in the afore-mentioned literature. For example, the nerve conduction block is preferably within the parameters disclosed in Solomonow, et al., "Control of Muscle Contractile Force through Indirect High-Frequency Stimulation", Am. J. of Physical Medicine, Vol. 62, No. 2, pp. 71-82 (1983). Particularly, the nerve conduction block is applied with electrical signal selected to block the entire cross-section of the nerve (e.g., both afferent, efferent, myelinated and nomnyelinated fibers) at the site of applying the blocking signal (as opposed to selected sub-groups of nerve fibers or just efferent and not afferent or visa versa) and, more preferably, has a frequency selected to exceed the 200 Hz threshold frequency described in Solomonow et al. Further, more preferred parameters are a frequency of 500 Hz (with other parameters, as non-limiting examples, being amplitude of 4 mA, pulse width of 0.5 msec, and duty cycle of 5 minutes on and 10 minutes off). As will be more fully described, the present invention gives a physician great latitude in selected pacing and blocking parameters for individual patients.

For bulimic, obese, or compulsive overeating patients, the device can be programmed so that when triggered, vagal activity is blocked and the patient's appetite is suppressed by a feeling of fullness (satiety). In some embodiments, manual activation by the patient is desirable, but because the psychological pattern is difficult to control, the use of circadian programming and detection of overeating by measuring quantity of food consumed during a given interval serves as an important backup in the therapeutic modality.

As discussed above, the impulse generator may also be activated manually by the patient by any of various means by appropriate implementation of the device. These techniques include the patient's use of an external magnet, or of an external RF signal generator, or tapping on the surface overlying the impulse generator, to activate the impulse generator and thereby cause the application of the desired modulating signal to the electrodes. Upon experiencing the compulsive craving, the overweight, obese or bulimic patient can simply voluntarily activate the impulse generator. If the patient fails to act, the automatic detection of the overeating and consequent application of the necessary therapy will take place through modulation of vagal activity to produce the sensation of satiety.

Another form of treatment of may be implemented by programming the impulse generator to periodically deliver the vagal activity modulation productive of satiety at programmed intervals between prescribed normal mealtimes. This will tend to reduce excessive snacking between meals, which may otherwise be of insufficient quantity within a preset time interval to trigger automatic delivery of the therapy.

The electronic energization package may, if desired, be primarily external to the body. An RF power device can provide the necessary energy level. The implanted components could be limited to the lead/electrode assembly, a coil and a DC rectifier. With such an arrangement, pulses programmed with the desired parameters are transmitted through the skin with an RF carrier, and the signal is thereafter rectified to regenerate a pulsed signal for application as the stimulus to the vagus nerve to modulate vagal activity. This would virtually eliminate the need for battery changes.

However, the external component transmitter must be carried on the person of the patient, which is inconvenient. Also, detection is more difficult with a simple rectification system, and greater power is required for activation than if the system were totally implanted. In any event, a totally implanted system is expected to exhibit a relatively long service lifetime, amounting potentially to several years, because of the relatively small power requirements for most treatment applications. Also, as noted earlier herein, it is possible, although considerably less desirable, to employ an external impulse generator with leads extending percutaneously to the implanted nerve electrode set. The major problem encountered with the latter technique is the potential for infection. Its advantage is that the patient can undergo a relatively simple procedure to allow short term tests to determine whether the condition associated with excess weight of this particular patient is amenable to successful treatment. If it is, a more permanent implant may be provided.

Signal Frequency

In some embodiments, the signal has a frequency of at least 200 Hz and up to 5000 Hz. In other embodiments, the signal is applied at a frequency of about 500 to 5000 Hz. Applicant has determined a most preferred blocking signal has a frequency of 3,000 Hz to 5,000 Hz or greater applied by two or more bi-polar electrodes. Such a signal has a preferred pulse width of 100 micro-seconds (associated with a frequency of 5,000 Hz). It is believed this frequency and pulse width best avoid neural recovery from blocking and avoid repolarization of the nerve by avoiding periods of no signal in the pulse cycle. A short "off" time in the pulse cycle (e.g., between cycles or within a cycle) could be acceptable as long as it is short enough to avoid nerve repolarization. The waveform may be a square or sinusoidal waveform or other shape. The higher frequencies of 5,000 Hz or more have been found, in porcine studies, to result in more consistent neural conduction block. Kilgore, et al., "Nerve Conduction Block Utilizing High-Frequency Alternating Current", Medical & Biological Engineering & Computing, Vol. 24, pp. 394-406 (2004). Preferably the signal is bi-polar, bi-phasic delivered to two or more electrodes on a nerve.

In some embodiments, a signal amplitude of 0.5 to 8 mA is adequate for blocking. Other amplitudes may suffice. Other signal attributes can be varied to reduce the likelihood of accommodation by the nerve or an organ. These include altering the power, waveform or pulse width.

Location of Signal Application

Electrodes can be positioned at a number of different sites and locations on or near the vagus nerve. In some embodiments, the electrode is positioned to apply a signal to a branch or trunk of the vagus nerve. In other embodiments, the electrode is positioned to apply a signal to an anterior trunk, posterior trunk or both. The electrode may also be positioned to apply a signal to an organ in proximity to the vagus nerve such as the esophagus or stomach. In some embodiments, the electrode is positioned to apply an electrical signal to the vagus nerve at a location near or distal to the diaphragm of the subject.

For example, FIG. 2 illustrates placement of a blocking electrode. Referring to FIG. 2, the baseline vagal activity is illustrated by the solid line of the proximal vagus nerve segment VNP. The remainder of the vagus and enteric nervous system are shown in reduced thickness to illustrate down-regulation of tone. The pancreo-biliary output (and resulting feedback) is also reduced. In FIG. 2, the blocking electrode BE is shown high on the vagus relative to the GI tract innervation (e.g., just below the diaphragm), the sole blocking electrode could be placed lower (e.g., just proximal to pancreo/biliary innervation VN5). Blocking of the entire vagus as described above can be used to down-regulate the vagus for various benefits including treating a condition associated with excess weight.

In other embodiments, alternative designs for placing electrodes on or near the vagus nerve in a region of the esophagus E either above or below the diaphragm are provided. Two paired electrodes may connect to a pulse generator for bi-polar pacing. In other embodiments, a portion of the vagus nerve VN is dissected away from the esophagus E. An electrode is placed between the nerve VN and the esophagus E. The electrode is placed overlying the vagus nerve VN on a side of the nerve opposite electrode and with electrodes axially aligned (i.e., directly across from one another). Not shown for ease of illustration, the electrodes may be carried on a common carrier (e.g., a PTFE or silicone cuff) surrounding the nerve VN. Other possible placements of electrodes are described herein US 2005/0131485 published Jun. 16, 2005, which patent publication is hereby incorporated by reference.

While any of the foregoing electrodes could be flat metal pads (e.g., platinum), the electrodes can be configured for various purposes. In an embodiment, an electrode is carried on a patch. In other embodiments, the electrode is segmented into two portions both connected to a common lead and both connected to a common patch. A flexible patch permits articulation of the portions of the electrodes to relieve stresses on the nerve VN.

Signal Type and Timing

Selection of a signal that downregulates neural activity and/or allows for recovery of neural activity can involve selecting signal type and timing of the application of the signal. For example, with an electrode conduction block, the block parameters (signal type and timing) can be altered by the impulse generator and can be coordinated with the pacing signals to block only during pacing. A representative blocking signal is a 500 Hz signal with other parameters (e.g., timing and current) matched to be the same as the pacing signal. The precise signal to achieve blocking may vary from patient to patient and nerve site. The precise parameters can be individually tuned to achieve neural transmission blocking at the blocking site.

In some embodiments, the signal has a duty cycle including an ON time during which the signal is applied to the nerve followed by an OFF time during which the signal is not applied to the nerve.

In some embodiments, subjects receive an implantable impulse generator 104. (FIG. 3) The electrodes 212, 212a are placed on the anterior vagus nerve AVN and posterior vagus nerve PVN just below the patient's diaphragm. The coil 102 is placed on the patient's skin overlying the implanted receiving coil 105. The external component 101 can be programmed for various signal parameters including options for frequency selection, pulse amplitude and duty cycle. The frequency options include 2500 Hz and 5000 Hz (both well above a threshold blocking frequency of 200 Hz). The vast majority of treatments are at 5,000 Hz, alternating current signal, with a pulse width of 100 microseconds. The amplitude options are 1-8 mA. Duty cycle could also be controlled. A representative duty cycle is 5 minutes of blocking frequency followed by 5 minutes of no signal. The duty cycle is repeated throughout use of the device.

FIG. 21 shows a typical duty cycle. Each ON time includes a ramp-up where the 5,000 Hz signal is ramped up from zero amperes to a target of 8 mA. Each ON time further includes a ramp-down from full current to zero current at the end of the ON time. For about 50% of the patients, the ramp durations were 20 seconds and for the remainder the ramp durations were 5 seconds. In some embodiments, the on time is elected to have a duration of no less than 30 seconds or no more than 180 seconds or both.

The use of ramp-ups and ramp-downs are conservative measures to avoid possibility of patient sensation to abrupt application or termination of a full-current 5,000 Hz signal. An example of a ramp-up for a high frequency signal is shown in U.S. Pat. No. 6,928,320 to King issued Aug. 9, 2005.

In some embodiments, a mini duty cycle can be applied. In an embodiment, a mini duty cycle comprises 180 millisecond periods of mini-ON times of 5,000 Hz at a current which progressively increases from mini-ON time to mini-ON time until full current is achieved (or progressively decreases in the case of a ramp-down). Between each of such mini-ON times, there is a mini-OFF time which can vary but which is commonly about 20 milliseconds in duration during which no signal is applied. Therefore, in each 20-second ramp-up or ramp-down, there are approximately one hundred mini-duty cycles, having a duration of 200 milliseconds each and each comprising approximately 180 milliseconds of ON time and approximately 20 milliseconds of OFF time.

Normally a patient would only use the device while awake. The hours of therapy delivery can be programmed into the device by the clinician (e.g., automatically turns on at 7:00 AM and automatically turns off at 9:00 PM). In the RF-powered version of the impulse generator, use of the device is subject to patient control. For example, a patient may elect to not wear the external antenna. The device keeps track of usage by noting times when the receiving antenna is coupled to the external antenna through radio-frequency (RF) coupling through the patient's skin.

In some cases, loss of signal contact between the external component 101 and implanted impulse generator 104 due occurs in large part to misalignment between coils 102, 105. (See FIG. 8). It is believed coil misalignment results from, at least in part, changes in body surface geometry throughout the day (e.g., changes due to sitting, standing or lying down). These changes can alter the distance between coils 102, 105, the lateral alignment of the coils 102, 105 and the parallel alignment of the coils 102, 105.

Figure 7:
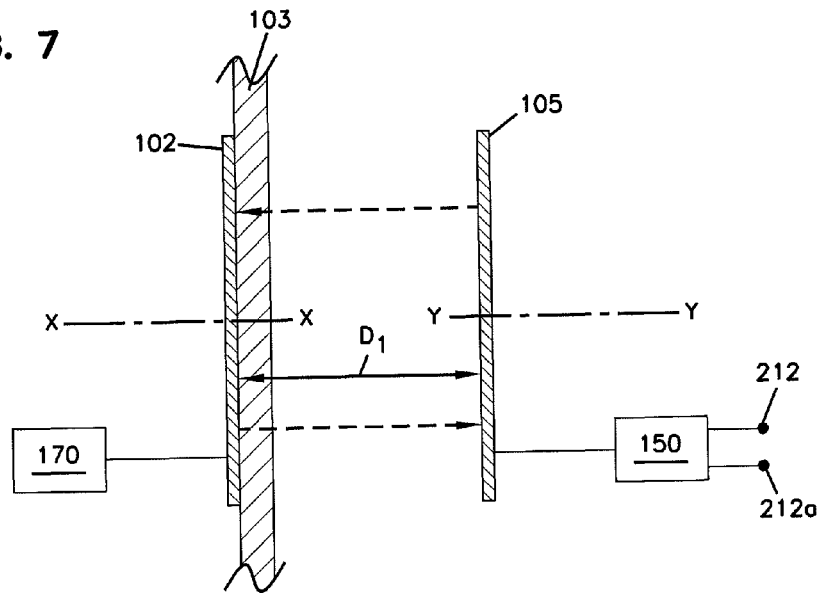
FIG. 7 is a side elevation schematic view of an external coil in a desired alignment over an implanted coil.

FIG. 7 illustrates a desired alignment. Coil 105 is implanted beneath the skin 103 at a preferred depth $D_1$ (e.g., about 2 cm to 3 cm beneath the skin 103), and with a plane of the coil 105 parallel to the surface of the skin 103. Each coil 102, 105 is a circular coil surrounding a central axis X-X and Y-Y. As shown in FIG. 7, in an ideal alignment, the axes X-X, Y-Y are collinear so that there is no lateral offset of the axes X-X, Y-Y and the coils 102, 105 are parallel. Such an alignment may be attained when the external coil 102 is applied when the patient is lying flat on his back.

Figure 8:
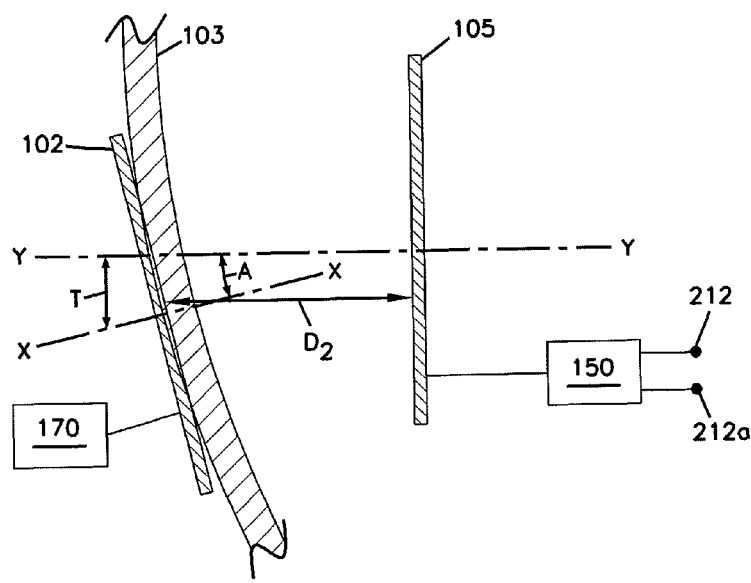
FIG. 8 is the view of FIG. 7 illustrating misalignment of the external and internal coils resulting from changes in patient posture.

FIG. 8 illustrates misalignment between the coils 102, 105 resulting from posture changes. When the patient stands, excess fat may cause the skin 103 to roll. This increases the spacing between the coils 102, 105 to increase to a distance $D_2$. Also, the axes X-X and Y-Y may be laterally offset (spacing T) and at an angular offset A. These changes may be constantly occurring throughout the day. As a result of coil misalignment, there may be a significant variance in the power received by the implanted coil 105. In the case of an implant receiving both power and command signals, in extreme cases, the power of a signal received by the implanted circuit 150 may be so weak or the communication link between the external component 101 and impulse generator 104 may be so poor that therapy is lost. Misalignment can be detected by the device and alignment of the coils adjusted to ensure that the signals are restored. The device may include a notification to the patient or physician if there has been a misalignment.

In some embodiments, the external component 101 can interrogate the impulse generator 104 for a variety of information. In some embodiments, therapy times of 30 seconds to 180 seconds per duty cycle are preferred to therapy times of less than 30 seconds per duty cycle or greater than 180 seconds per duty cycle.

During a 10 minute duty cycle (i.e., intended 5 minutes of therapy followed by a 5 minute OFF time), a patient can have multiple treatment initiations. For example, if, within any given 5-minute intended ON time, a patient experienced a 35-second ON time and 1.5 minute actual ON time (with the remainder of the 5-minute intended ON time being a period of no therapy due to signal interruption), the patient could have two actual treatment initiations even though only one was intended. The number of treatment initiations varies inversely with length of ON times experienced by a patient.

The flexibility to vary average vagal activity gives an attending physician great latitude in treating a patient. For example, in treating obesity, the blocking signal can be applied with a short "no blocking" time to reduce weight as rapidly as possible. If the patient experiences discomfort due to dysmotility, the duration of the "no blocking" period can be increased to improve patient comfort. Also, the reduction of enzyme production can result in decreased fat absorption with consequential increase of fat in feces. The blocking and no blocking duration can be adjusted to achieve tolerable stool (e.g., avoiding excessive fatty diarrhea). The control afforded by the present invention can be used to prevent the enteric nervous system's assumption of control since vagal activity is not completely interrupted as in the case of a surgical and permanent vagotomy.

While patient weight loss and comfort may be adequate as feedback for determining the proper parameters for duration of blocking and no blocking, more objective tests can be developed. For example, the duration of blocking and no blocking can be adjusted to achieve desired levels of enzyme production and nutrient digestion. In one example of drug therapy for obesity, orlistat blocks the action of lipase. Lipase is a fat-digesting enzyme. As a consequence of this reduction in lipase, the fat content of feces increases. It is generally regarded as desirable to modulate drug intake so that fecal fat does not exceed 30% of ingested fat. Similarly, the blocking and no blocking durations can be modulated to achieve the same result. Such testing can be measured and applied on a per patient basis or performed on a statistical sampling of patients and applied to the general population of patients.

In some embodiments, a sensing electrode SE (not shown in the drawings) is added to the system to monitor vagal activity as a way to determine how to modulate the block and no block durations. While sensing electrode can be an additional electrode to blocking electrode, it will be appreciated a single electrode could perform both functions. The sensing and blocking electrodes can be connected to a coil as shown in FIG. 3. Such a coil is the same as coil 102 previously described with the additive function of receiving a signal from sensing electrode (which yields the actual vagal activity of the graph of FIG. 6). When the sensing electrode SE (not shown in the drawings) yields a signal representing a targeted maximum vagal activity or tone (e.g., 50% of baseline as shown in FIG. 6) the controller with the additive function of receiving a signal from sensing electrode energizes the blocking electrode BE with a blocking signal. As described with reference to controller coil 102, controller with the additive function of receiving a signal from sensing electrode can be remotely programmed as to parameters of blocking duration and no blocking duration as well as targets for initiating a blocking signal.

The apparatus and method described herein use recovery of the vagus nerve to control a degree of down-regulation of vagal activity. This gives a physician enhanced abilities to control a patient's therapy for maximum therapeutic effectiveness with minimum patient discomfort. Therefore, while obesity is particularly described as a preferred treatment, the vagal neural block of the present invention can be used as treatment for other conditions associated with excess weight.

Agents that Alter the Energy Balance of the Subject

The disclosure provides methods for treating a condition associated with excess weight that include administering to a subject a composition comprising an agent that alters an energy balance in a subject. The disclosure also provides systems and methods that provide for selecting an agent that alters energy balance of the subject based on the health profile of the subject and the side effects of the agent.

In some embodiments, the agent will increase energy expended and/or decrease the amount of energy consumed. Agents that alter energy balance in a subject are known to have certain characteristics, for example, some agents enhance the sensation of satiety, other agents decrease appetite (anorexic), others block the absorption of fat or other nutrients, others inhibit enzymes that digest fat, some agents are thermogenic, and some have combinations of effects.

Several pathways are known to affect energy balance. Pathways include gut-hypothalamic axis (e.g. ghrelin), gut-hindbrain axis (e.g. vagus nerve), peripheral tissue (adipose tissue, skeletal muscle)-hypothalamic axis (e.g. leptin), and hypothalamic-hindbrain axis (neural projections). In particular, the hypothalamus (forebrain) and the area postrema (hindbrain) are 2 regions of the central nervous system which are thought to play orchestrating roles in the human energy homeostasis. It has been documented that there are neural connections between these two regions enabling communications and complimentary, as well as, redundant effects on body energy balance. Numerous hormones, enzymes, neurotransmitters, and other mediators are released from different parts of these pathways and can have influences on these regions of the central nervous system. These interactions, in turn, ultimately produce orexigenic or anorexic behavior thereby altering the energy balance of a patient. Utilization of distinct treatment modalities that involve different parts of these pathways and brain regions, thus altering the communication between the hypothalamus and area postrema, may be of importance in combinatorial therapy that is highly effective, robust, and durable.

Agents that alter energy balance can be selected based on an ability to complement treatment of applying a signal to downregulate neural activity of the vagal nerve. Drugs that have been approved by the FDA to treat obesity include sibutramine and orlistat for long term use; and phentermine for short term use. However, the excess weight loss associated with administration of these drugs is limited to a maximum of about 10% when compared with loss due to diet and exercise alone. As described herein, an agent is selected that may provide a complementary or synergistic effect with the application of signal to modulate neural activity on the vagus nerve. A synergistic or complementary effect can be determined by determining whether the patient has an increase in excess weight loss as compared to one or both treatments alone. In some embodiments, agents that act at a different site (e.g. hypothalamus or pituitary) or through a different pathway may be selected for use in the methods described herein. Agents that complement treatment are those that include a different mechanism of action for affecting the excess weight of the subject.

An agent may also or in addition be selected to administer that may have undesirable side effects at the recommended dosage that prevents use of the agent, or that prevents compliance by the patient. In addition, patients that have excess weight as well as hypertension, cardiac conditions, liver disease, or renal disease may not be able to tolerate treatment with one or more of the agents at the recommended dosage due to adverse side effects. Agents that have undesirable side effects include fenfluramine, and dexfenfluramine which have been shown to have adverse effects on blood pressure and to be associated with valvular heart disease. Other drugs such as bupropion can cause seizures. Drugs that inhibit fat absorption, such as orlistat, can cause diarrhea, soft and oily stools, and flatulence. Other drugs may cause central nervous system symptoms such as anxiety, cognitive deficits, depression, and/or nervousness.

Combining administration of a drug with undesirable side effects with modulating neural activity on the vagus nerve may allow for administration of the drugs at a lower dose thereby minimizing the side effects. In addition, a drug may be selected that has altered pharmacokinetics when absorption is slowed by a delay in gastric emptying due to neural downregulation as described herein. In other embodiments, the recommended dosage may be lowered to an amount that has fewer adverse side effects. In some embodiments, the therapeutic window may be increased. In some embodiments, a drug that may be useful for short term use may be administered for long term use at the lowered dosage. For example, a drug such as rimonabant at 20 mg per dose may be lowered to a 5 mg dose and still be effective for weight loss. In embodiments, it is expected that the recommended dosage may be able to be lowered at least 25%. In other embodiments, the dosage can be lowered to any percentage of at least 25% or greater of the recommended dose. In some embodiments, the dosage is lowered at least 25, 30, 35, 40, 45, 50, 55, 60, 65, 70, 75, 80, 85, 90, 95, or 100% of the recommended dosage.

In an embodiment, a method provides a treatment for a condition associated with excess weight such as obesity. A method comprises selecting a drug useful for treating excess weight or obesity and having a recommended dosage for efficacy where a patient is likely to experience disagreeable side effects at said recommended dosage; and treating the patient with a concurrent treatment comprising: applying an intermittent neural block to a vagus nerve of the patient at multiple times per day and over multiple days with the block selected to down-regulate afferent and/or efferent neural activity on the nerve and with neural activity restoring upon discontinuance of said block; and administering said drug to the patient at a dosage less than said recommended dosage. In some embodiments, the effective dosages for treating a condition associated with excess weight for such a patient are associated with disagreeable side effects contributing to said patient not complying with a drug treatment. In some embodiments, patients are those that have an eating disorder, hypertension, cardiac conditions, liver, or renal disorder and may not be able to tolerate treatment with one or more of the agents that alter energy balance at the recommended dosage due to adverse side effects.

Agents that affect the hypothalamic or neuroendocrine function such as ghrelin, ghrelin agonists, ghrelin antagonists, leptin agonist, leptin antagonists, ciliary neurotrophic factor (CNTF), CNTF analogues, amylin, and amylin analogues may complement effects on the vagus nerve. In addition, agents that enhance the sensation of satiety and reduce appetite and act on neurotransmitters in the brain may complement the effects of neural downregulation on the vagus nerve. Such agents include neurotransmitter releasers, inhibitors of the uptake of serotonin, norepinephrin, and dopamine. These agents include, for example, sibutramine, fenfluramine, phentermine, dexphenfluoramine, fluoxetine, and bupropion. Agents that are thermogenic increase energy expenditure of the patient and would have a complementary effect to that of modulating the neural activity of the vagus nerve. These agents include, for example, sibutramine, leptin, leptin agonists, leptin analogues, CNTF, and CNTF analogues. Agents that suppress appetite and enhance the feeling of satiety include incretins including GLP-1, PYY, CKK, and oxyntomodulin.

In the methods of the disclosure, an anorexic agent may be administered. Several anorexic agents are known to those of skill in the art. Anorexic agents include phentermine, fenfluramine, dexfenfluramine, endocannabinoid receptor antagonists, ghrelin antagonists, orexin antagonists, somatostatin receptor agonist, GLP-1, PYY, and cholecystokinin agonists. Endocannaboid receptor antagonists are known and include rimonabant. Phentermine has been approved for short term treatment of obesity.

Thermogenic agents are attractive as they increase the energy expenditure of the subject. Leptin, for example, may reduce calorie intake and increases energy expenditure through action on the sympathetic nerve system. Other agents that have thermogenic characteristics include sibutramine, leptin, leptin agonist, a leptin analogue, ciliary neurotrophic factor (CNTF), and a CNTF analogue. Axokine is a CNTF analogue that has been shown to promote weight loss. Sibutramine has been approved for long term treatment of obesity.

Agents that inhibit fat absorption are more likely to have effects similar to that of modulating neural activity of the vagus nerve rather than complementary effects. Even though the action of agents that inhibit fat absorption may not be complementary to downregulation of vagal nerve activity, they have undesirable side effects that may contribute to a lack of patient compliance. Such side effects include diarrhea, flatulence and loose stools. Some agents inhibit the action of lipases that break down fat in ingested food. Agents that inhibit fat absorption include orlistat or a lipin inhibitor. Orlistat has been approved for long term treatment of obesity.

Agents that enhance satiety through a CNS pathway, such as a hypothalamic or neuroendocrine pathway, would have effects complementary to those due to treatment by modulating neural activity on the vagus nerve. Agents that enhance satiety include somatostatin receptor agonists, GLP-1 agonists, GLP-1 variants, peptide PYY, POMC agonists, neuropeptide Y inhibitors, topiramate, tegretol, bupropion, naltrexone, zonisamide, amylin, amylin analogues, and oxyntomodulin. Pramlitidine is an amylin analogue that has shown effectiveness in clinical trials for weight loss. Exendin-4 is a potent and long lasting GLP-1 analogue and agonist of GLP-1. Liraglutide is also a long acting analogue of GLP-1. Administration of PYY increases propiomelanocortin activity and has been shown to result in decreased food consumption. Oxyntomodulin suppresses appetite and food intake.

Sequences for the polypeptides such as GLP-1, ghrelin, leptin are known to those of skill in the art and are described in publicly available databases. Representative sequences are: Leptin (gI 1469860 and gI4557715); ghrelin (gI 37183224); POMC (GI 190188); GLP-1 (gI 125987831 (P01275)); CKKB receptor (gI 417029); CNTF (gI 633830, gI 825643, gI116585); PYY (gI 71361686, gI 1172776); orexin (gI 4557635); somatostatin receptor (gI 431095, gI 307430) and amylin (gI 457131, gI 4557655).

In some embodiments, the agents that alter the energy balance in the subject do not include prokinetic agents. Prokinetic agents are drugs that enhance motor activity of the smooth muscle characteristic of GI tract. These agents have been used for treating gastroesophageal reflux disease (GERD) and are beneficial for improving the strength of esophageal peristalsis, the resting pressure of the LES, the strength of gastric contractions, and improving gastric motility. Recently, cisapride, the most commonly prescribed prokinetic agent, has been withdrawn from the US market because of rare, but life-threatening cardiac arrhythmias. Metoclopramide, another prokinetic agent proven effective for GERD, is frequently associated with unpleasant side effects. In other embodiments, prokinetic agents may be used as an agent that alters energy balance in a subject but a dosage that provides for alleviating a symptom of the eating disorder while minimizing the side effects.

In some embodiments, the patient has a condition associated with excess weight including obesity, compulsive eating, and/or bulimia. In some embodiments, a patient may be selected that is not yet obese but is overweight. Excess weight of at least 10 pounds or 10-20 pounds is associated with adverse health effects. Overweight and obesity classifications include those determined by body mass index (BMI) (calculated as weight in kilograms divided by the square of height in meters). For example, normal weight: BMI=18.5-24.9; overweight: BMI=25.0-29.9; obesity-class 1: BMI=30.0-34.9; obesity-class 2: BMI=35.0-39.9; obesity-class 3: BMI≥30.0).

Of course these ranges may vary given the height, gender, and age of the subject. In other embodiments, the patient at least has a body mass index (BMI) of at least 25 or greater. In other embodiments, the patient has a BMI of at least 27 to about 30 and also has other health conditions such as hypertension, diabetes, cardiovascular disease, liver disease, and/or renal disease. In other embodiments, the patient is overweight at least 10 pounds and/or has a condition such as type II diabetes, asthma, arthritis, hypertension, high cholesterol, and/or cardiovascular disease.

Dosages for administration to a subject can readily be determined by one of skill in the art. Guidance on the dosages can be found, for example, by reference to other drugs in a similar class of drugs. For example, dosages have been established for any of the approved drugs or drugs in clinical trials and the range of dose will depend on the type of drug. For example, pramlintide dosages range from about 240 micrograms up to 720 micrograms per day. A dosage of sibutramine of 5 to 20 mg per day is recommended.

Dosages associated with adverse side effects are known or can also be readily determined based on model studies. For example, dosages of 30 mg per day or greater of fenfluramine in combination with dexphenflouramine were associated with valvular heart conditions. Risk of seizures and increase in blood pressure with bupropion treatment increases at doses of 300 mg per day or greater. A determination of the effective doses to achieve excess weight loss while minimizing side effects can be determined by animal studies.

Agents that alter the energy balance will be formulated, dosed, and administered in a fashion consistent with good medical practice. Factors for consideration in this context include the particular disorder being treated, the particular mammal being treated, the clinical condition of the individual patient, the age of the patient, other medications that the patient is taking, the cause of the disorder, the site of delivery of the agent, the method of administration, the scheduling of administration, and other factors known to medical practitioners. The agent need not be, but is optionally formulated with one or more agents currently used to prevent or treat the disorder in question. The effective amount of such other agents depends on the amount of agent that alters an energy balance of the subject present in the formulation, the type of disorder or treatment, and other factors discussed above. These are generally used in the same dosages and with administration routes as used hereinbefore or about from 1 to 99% of the heretofore employed dosages.

The agent that alters energy balance of the subject can be administered at the same time that the subject is receiving a therapy signal treatment, after therapy signal treatment has been administered and is ongoing, when therapy signal treatment is providing for maintenance of weight loss. For example, the implantable device can be implanted and the subject undergo therapy for a period of at least 1 month to determine the rate of excess weight loss using the device. The rate and amount of excess weight loss using the implantable device can be determined and if weight loss is not adequate (e.g., less than 1% excess weight loss) then the therapy cycle parameters may be adjusted and/or an agent that alters energy balance can be administered. In most cases, the implantable device will deliver therapy for a period of time before the agent is administered to the subject. An agent that alters energy balance may be administered in those patients that appear to be nonresponders or intermediate responders.

Therapeutic formulations comprising the agent are prepared for storage by mixing the agent having the desired degree of purity with optional physiologically acceptable carriers, excipients or stabilizers (*Remington's Pharmaceu-* tical Sciences 16th edition, Osol, A. Ed. (1980)), in the form of aqueous solutions, lyophilized or other dried formulations. Acceptable carriers, excipients, or stabilizers are nontoxic to recipients at the dosages and concentrations employed, and include buffers such as phosphate, citrate, histidine and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

The formulation herein may also contain more than one active compound as necessary for the particular indication being treated. In certain such embodiments, the compounds have complementary activities that do not adversely affect each other. Such molecules are suitably present in combination in amounts that are effective for the purpose intended.

The therapeutic agent is/are administered by any suitable means, including parenteral, subcutaneous, orally, intradermal, intraperitoneal, and by aerosol. Parenteral infusions include intramuscular, intravenous, intraarterial, intraperitoneal, or subcutaneous administration. Pumps may be utilized as well as drug eluting devices and capsules.

EXAMPLE 1

A. VBLOC-I Obesity Study

In early 2006, Assignee began a human pilot study ("VBLOC-I) to evaluate an obesity treatment according to the present invention. The inclusion criteria of the VBLOC-I study required the patient have a body mass index (BMI) in a range between 35 and 50 (±10%). A BMI>30 is regarded as obese. A BMI>35 is generally regarded as morbidly obese.

After receiving the impulse generator 104, (FIG. 3) the device was inactive for a two-week post-surgery healing period. Thereafter, the therapy was initiated. Patients were followed at regular periods throughout the study. The study was designed to measure efficacy at multiple time points post-implant. Efficacy is measured as the amount of excess weight loss (EWL) experienced by the patient. Excess weight is the difference between the patient's actual weight and ideal weight. The patient's excess weight is determined prior to surgery ("baseline") as well as at multiple time points post-implantation. The EWL is the weight loss expressed as a percent of the baseline excess weight.

Patients enrolled in the VBLOC-I study received an impulse generator 104. All patients in the VBLOC-I study received an RF-powered version of the impulse generator. The electrodes 212, 212a were placed on the anterior vagus nerve AVN and posterior vagus nerve PVN just below the patient's diaphragm.

The coil 102 was placed on the patient's skin overlying the implanted receiving coil 105. The external component 101 can be programmed for various signal parameters including options for frequency selection, pulse amplitude and duty cycle. The frequency options include 2500 Hz and 5000 Hz (both well above a threshold blocking frequency of 200 Hz). The vast majority of treatments were at 5,000 Hz, alternating current signal, with a pulse width of 100 microseconds. The amplitude options are 1-8 mA. Duty cycle could also be controlled. A representative duty cycle is 5 minutes of blocking frequency followed by 5 minutes of no signal. The duty cycle was repeated throughout use of the device.

Normally a patient would only use the device while awake. The hours of therapy delivery can be programmed into the device by the clinician (e.g., automatically turns on at 7:00 AM and automatically turns off at 9:00 PM). In the RF-powered version of the impulse generator, use of the device is subject to patient control. For example, a patient may elect to not wear the external antenna. The device keeps track of usage by noting times when the receiving antenna is coupled to the external antenna through radio-frequency (RF) coupling through the patient's skin.

B. Weight Loss Data

Figure 9:
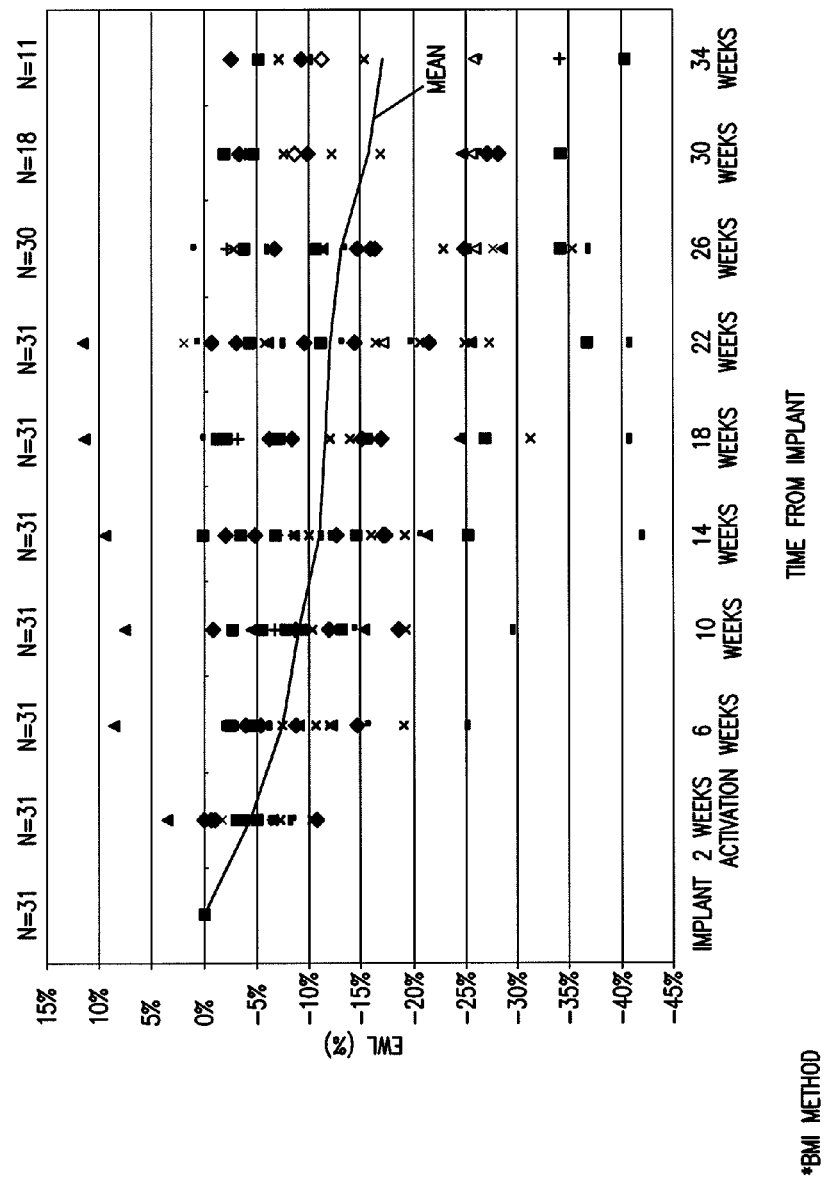
FIG. 9 is a scatter graph of patients treated with a vagal down-regulation procedure and showing excess weight loss (EWL) over time for each patient and showing a mean EWL.

As would be expected in a human weight loss study, patients vary significantly in their response to treatment. However, overall weight loss has been very promising. Of thirty-one patients entered in the study, patients experienced an average weight loss of 16% after 34 weeks. FIG. 9 is an example of a scatter graph of all patients not otherwise excluded. "Excluded" means patient data was excluded for reasons of not using the device for significant periods or equipment failure. (E.g. Two patients were excluded from the data. Their exclusion was due to their extended periods of non-use of the device and questionable impedance data indicating therapy was not being delivered to the patient).

In FIG. 9, the vertical axis is the excess weight loss relative (as a percent of baseline weight). The horizontal axis is the number of weeks following treatment. "Maestro Implant" is the surgery date. "2 Weeks Maestro Activation" is the date of device activation following a 2-week post-surgery healing period. The remaining dates on the horizontal axis are post-surgery follow-up dates measured from date of surgery "Maestro Implant".

The data are very encouraging. In any human treatment study, one expects patient-to-patient outcome variability. That is reflected in the data of FIG. 9. During the VBLOC-I study, patients were intended to receive a therapy dose of 5 minutes of electrical signal followed by 5 minutes of no signal. This duty cycle was to be repeated throughout the day.

FIG. 21 shows a typical duty cycle. Each ON time includes a ramp-up where the 5,000 Hz signal is ramped up from zero amperes to a target of 8 mA. Each ON time further includes a ramp-down from full current to zero current at the end of the ON time. For about 50% of the patients, the ramp durations were 20 seconds and for the remainder the ramp durations were 5 seconds.

The use of ramp-ups and ramp-downs are conservative measures to avoid possibility of patient sensation to abrupt application or termination of a full-current 5,000 Hz signal. An example of a ramp-up for a high frequency signal is shown in U.S. Pat. No. 6,928,320 to King issued Aug. 9, 2005.

Not shown in the drawings, each ramp-up and ramp-down in the VBLOC-I study was broken into mini-duty cycles consisting of many imbedded OFF times of very short duration. While the mini-duty cycle was not completely uniform, it is approximated by 180 millisecond periods of mini-ON times of 5,000 Hz at a current which progressively increases from mini-ON time to mini-ON time until full current is achieved (or progressively decreases in the case of a ramp-down). Between each of such mini-ON times, there is a mini-OFF time which can vary but which is commonly about 20 milliseconds in duration during which no signal is applied. Therefore, in each 20-second ramp-up or ramp-down, there are approximately one hundred mini-duty cycles, having a duration of 200 milliseconds each and each comprising approximately 180 milliseconds of ON time and approximately 20 milliseconds of OFF time.

Analyzing data recovered during the post-surgery follow-ups, it was noted that, frequently, patients did not receive the full 5-minute dose. It was determined this was primarily due to loss of signal contact between the external component 101 and implanted impulse generator 104 due in large part to misalignment between coils 102, 105.

It is believed coil misalignment results from, at least in part, changes in body surface geometry throughout the day (e.g., changes due to sitting, standing or lying down). These changes can alter the distance between coils 102, 105, the lateral alignment of the coils 102, 105 and the parallel alignment of the coils 102, 105.

FIG. 7 illustrates a desired alignment. Coil 105 is implanted beneath the skin 103 at a preferred depth $D_1$ (e.g., about 2 cm to 3 cm beneath the skin 103), and with a plane of the coil 105 parallel to the surface of the skin 103. Each coil 102, 105 is a circular coil surrounding a central axis X-X and Y-Y. As shown in FIG. 7, in an ideal alignment, the axes X-X, Y-Y are collinear so that there is no lateral offset of the axes X-X, Y-Y and the coils 102, 105 are parallel. Such an alignment may be attained when the external coil 102 is applied when the patient is lying flat on his back.

FIG. 8 illustrates misalignment between the coils 102, 105 resulting from posture changes. When the patient stands, excess fat may cause the skin 103 to roll. This increases the spacing between the coils 102, 105 to increase to a distance $D_2$. Also, the axes X-X and Y-Y may be laterally offset (spacing T) and at an angular offset A. These changes may be constantly occurring throughout the day. As a result of coil misalignment, there may be a significant variance in the power received by the implanted coil 105. In the case of an implant receiving both power and command signals, in extreme cases, the power of a signal received by the implanted circuit 150 may be so weak or the communication link between the external component 101 and impulse generator 104 may be so poor that therapy is lost.

Since such unintended signal interruption is undesirable, when an indication of such misalignment is detected, the device can and was realigned.

C. Observed Variations in Duty Cycle a. Length of ON Times

During patient follow-up visits in the VBLOC-I study, the external component 101 can interrogate the impulse generator 104 for a variety of information. From the collected data, a physician can determine how often the patient is receiving the intended therapy. For example, the physician can determine if a patient is receiving a full five minutes of an intended 5-minute therapy or only a portion (10 seconds, 1 minute, 4.5 minutes, etc).

Analysis of the collected data, showed that a range of actual therapy stood out as being surprisingly superior. Specifically, it was noted that therapy times of 30 seconds to 180 seconds per duty cycle were significantly superior to therapy times of less than 30 seconds per duty cycle or greater than 180 seconds per duty cycle.

Number of Therapeutic ON Times

During a 10 minute duty cycle (i.e., intended 5 minutes of therapy followed by a 5 minute OFF time), a patient can have multiple treatment initiations. For example, if, within any given 5-minute intended ON time, a patient experienced a 35-second ON time and 1.5 minute actual ON time (with the remainder of the 5-minute intended ON time being a period of no therapy due to signal interruption), the patient could have two actual treatment initiations even though only one was intended. The number of treatment initiations varies inversely with length of ON times experienced by a patient.

D. Statistical Analysis of Duty Cycle Data and Weight Loss

A statistical analysis of collected data from the VLOC-I study was performed. The primary analysis method employed was a mixed model, repeated measures regression analysis. This methodology is standard for longitudinal or serially collected data. In the VBLOC-I study, data on delivered therapy (actual ON times) and excess weight loss (EWL) were available for at least some of the patients at weeks 1, 2, 3, 4, 6, 8, 10, 12, 16, 20 and 24 post-therapy initiation (with therapy initiation being 2-weeks post implantation).

Data from a particular subject patient across follow-up visits were correlated, and the mixed model regression analysis effectively accounted for this correlation and avoided the situation whereby the effect size of a particular parameter was overestimated. This analysis essentially computed an average effect for each subject and averaged that effect across subjects, weighted according to the amount of information each subject was contributing.

a. Quartile Analysis

To facilitate an analysis, patients were grouped into quartiles based on the number of ON times experienced by a patient. For example, for any given follow-up period (e.g., 6 weeks post-therapy initiation corresponding to 8 weeks post-implantation), twenty-four patients may report for such follow-up (the numbers given here are hypothetical for ease of explanation). Interrogation of the patients' implants reveal the patients have a wide number of different therapy initiations (correlating inversely with a wide variety of ON time durations). Patients are divided into quartiles based on the number of ON times experienced by the patient. In the example given, Quartile 4 would be the six patients (i.e., 25%) having the most number of ON times. Quartile 1 would the six patients (i.e., 25%) having the fewest number of ON times.

A quartile analysis can be made using, among other options, a visit interval-defined quartile analysis or a subject-defined quartile analysis. A visit interval-defined quartile analysis was chosen. However, information is supplied below showing comparability of such analysis with a subject-defined quartile analysis.

b. Visit Interval-Defined Quartile Analysis

Figure 12:
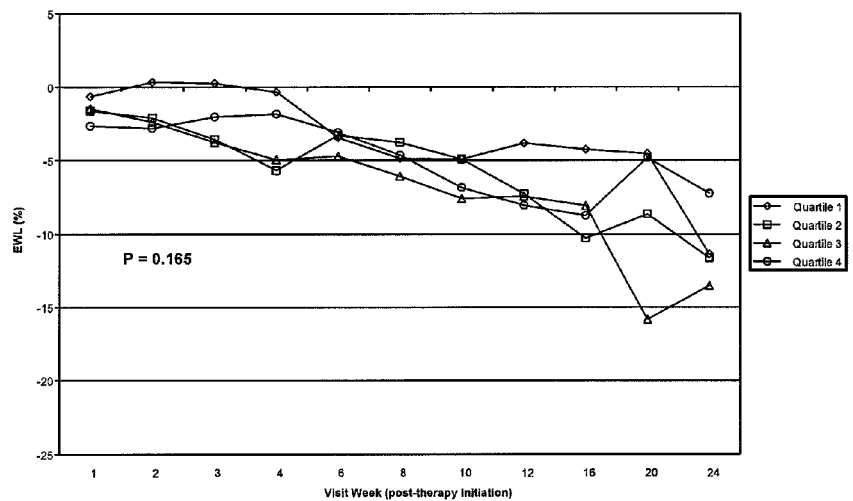
FIG. 12 is a graph similar to that of FIG. 10 for patients grouped into visit interval-defined quartiles based on frequency of occurrence of ON times with durations between 180 and 300 seconds.

In FIGS. 10-12, therapeutic ON time quartiles are defined according to visit intervals. These figures illustrate the effect of the number of ON times of a specific duration. In these figures, discrete ON time durations (i.e. 0-30 seconds (FIG. 10), 30-180 seconds (FIG. 11), and 180-300 seconds (FIG. 12)) are analyzed in a repeated measures regression model to determine the duration of ON time with the greatest effect on EWL.

In FIG. 10, there is a relationship between quartiles and EWL as represented by the statistically significant "p-value" of 0.001. (A "p-value" of less than 0.05 is generally regarded as significant since it represents a 95% confidence level that the data variations are attributable to non-random events).

However, the effect of this 0-30 second ON time is an order of magnitude less than that seen with therapeutic ON times of either 30-120 or 30-180 seconds (as discussed below) as shown by the parameter estimates of FIG. 17.

In FIG. 11, there is a strong relationship between quartiles of therapeutic ON times from 30-180 seconds and EWL as evidenced by the p-value of 0.004. This therapeutic ON time duration of 30-180 seconds (which includes, as a subset, ON time durations of 30-120 seconds (FIG. 13)), represents the ON time with the greatest effect on EWL.

In FIG. 12, there is no statistically significant quartile effect of therapeutic ON times from 180-300 seconds as shown by the relatively high p-value of 0.165. The frequency of longer duration ON times is inconsequential in terms of incremental EWL. There is no additional benefit of longer ON times, relative to shorter ON times, with respect to EWL.

Figure 13:
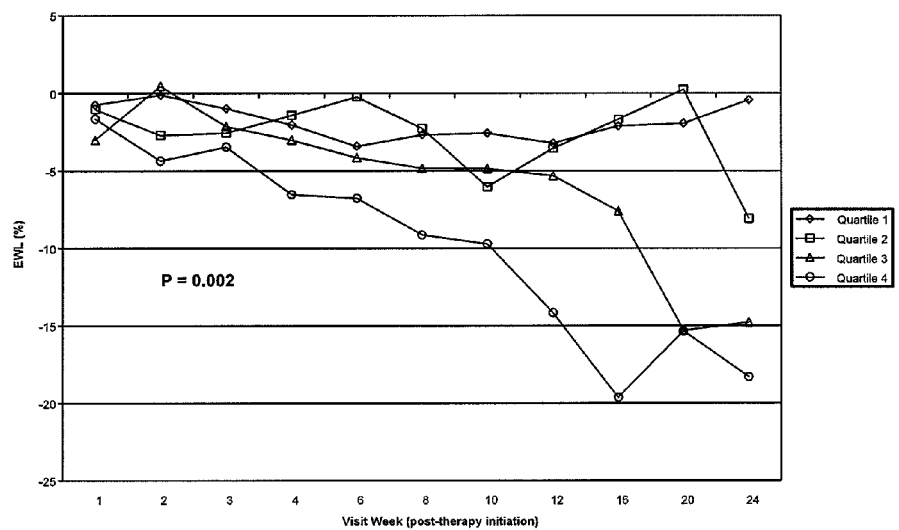
FIG. 13 is a graph similar to that of FIG. 10 for patients grouped into visit interval-defined quartiles based on frequency of occurrence of ON times with durations between 30 and 120 seconds.

FIG. 13 analyzes a subset (30-120 seconds) of the data of FIG. 6 (30-180 seconds). As with the analysis of 30-180 second therapeutic ON times (FIG. 6), there is a strong relationship between quartiles of ON times from 30-120 seconds and EWL as evidenced by the p-value of 0.002. This therapeutic ON time duration of 30-120 seconds represents the optimal combination of effect on EWL (and battery longevity for a battery powered implant).

c. Study Subject-Defined v. Visit Interval-Defined Quartile Analyses

In a visit interval-defined quartile analysis, subjects are allowed to move from one quartile to another over the follow-up period. The repeated measures analysis described above adequately accounted for the visit-to-visit movement by an individual subject from one quartile to another by isolating the effect of ON times to the interval preceding each study visit and calculating a slope across visits.

By allowing movement between quartiles across visits, the analysis addressed the fact that ON times were not necessarily consistent across all visits for an individual study subject. For instance, if an intermittent or inconsistent link developed during an interval between visits but was then corrected at the next visit, that individual subject might have a greater number of therapeutic ON times ($\geq$30 seconds) for the period of time with an inconsistent link compared with the period of time with consistent link. If ON times are associated with EWL, there would be a different effect on weight loss for the period of time with a greater frequency of therapeutic ON times compared with the period of time with consistent link.

Through the course of follow-up, that subject may have an average or low number of ON times and a different overall weight loss than was observed during the period of time with an inconsistent link. By allowing for movement across quartiles, we are able to account for such interval effects of ON times on EWL.

There is value, though, in also examining the cumulative frequency of therapeutic ON times through a certain follow-up visit (e.g. 20 weeks) and dividing subjects into quartiles according to the grand total number of ON times (corrected for total days on study). This analysis evaluates whether or not the cumulative (over 20 weeks) total number of therapeutic ON times has an effect on excess weight loss. The repeated measures approach in this instance adjusts for the within-patient correlation across follow-up visits, but does not take into account that a subject may have a variable frequency of ON times from one visit to another. That is, only the average frequency of ON times over the course of follow-up is considered. This type of analysis is "study subject-defined quartile analysis".

Study subject-defined and visit interval-defined quartile analyses are compared in FIGS. 14 and 15. In these analyses, "ON time" means an actual therapy time greater than or equal to 30 seconds. Quartiles are divided on the basis of frequency of ON times.

The p-value in these analyses is the significance of the effect across quartiles. This p-value not only incorporates a measure of linearity, but also effect size. A non-significant p-value would be an indication of no linear effect of therapeutic ON times on % EWL.

A similar effect is seen in both analyses. There is a generally linear effect of the number of ON times (according to quartile) and the percent EWL. The significance level for both analyses is statistically significant, though the more granular analysis (visit interval-defined quartiles) is more significant. Because the patient groups for the study subject-defined quartiles is determined according to the cumulative number of ON times over a fixed period of time (20 weeks), sample size is smaller (29 vs. 31 subjects) as data was not available at 20 weeks for two subjects.

Defining quartiles in the described manners yield similar results in terms of the effect of therapeutic ON times on excess weight loss. Evaluating subject-defined quartiles has confirmed the findings from the study visit interval-defined quartile analysis.

From a comparison of FIGS. 14 and 15, it was determined that the mixed model, repeated measures regression models are appropriate for both quartile-defined analyses. A strong, linear relationship exists between frequencies of therapeutic ON times greater than or equal to 30 seconds and excess weight loss in the VBLOC-I study population. Each of the two quartile analyses yield consistent results and conclusions, and are mutually confirmatory d. Additional Analysis FIGS. 16 and 17 graphically illustrate an alternative analysis showing the observed superiority of 30 to 180 seconds therapy per duty cycle versus other options within a 0 to 5 minute range. FIGS. 16 and 17 represent the parameter estimates associated with distinct ON time bins. A "bin" is an assignment of data. For example, "Bin 1" is defined as data associated with ON times of less than 30 seconds. The bins are reflected in Table 17.

Figures 16, 17:
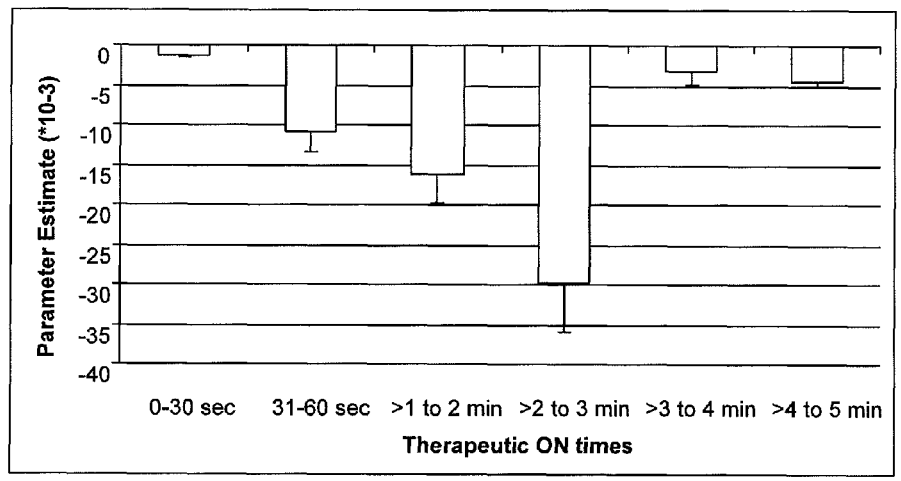
FIG. 16 is a graph illustrating efficacy as a function of therapeutic ON times.
FIG. 17 is a table illustrating the results of FIG. 16.

FIGS. 16 and 17 represent the parameter estimates associated with distinct ON time bins. Bins are retrospective groupings to permit analyzing the correlation, if any, between length of ON times and excess weight loss.

For each bin, a parameter estimate is given. These parameter estimates are from a mixed model, repeated measures regression analysis that estimates the effect of the cumulative number of ON times of a given duration over time. Such models and analyses are well known in statistics.

The parameter estimate represents the slope of the regression line, and a one-unit increase in the cumulative number of ON times for a particular bin is associated with a percent of excess weight loss equal to the parameter estimate for that ON time. For example, a 100 unit increase in the number of ON times from two to three minutes in duration is associated with a $-2.9\%$ EWL.

G. Conclusions from Statistical Analysis

From the foregoing, it was concluded that a greater number of initiations of therapeutic ON times during any given time period are associated with greater excess weight loss (EWL). This therapeutic effect is greatest with therapeutic ON times of either 30-180 seconds (p=0.004) or 30-120 seconds (p=0.002). Therapeutic ON time durations of 30-120 seconds represent the optimal combination of effect on EWL and battery longevity. As a matter of conjecture, the central nervous system may accommodate to a loss of vagal neural activity after about 180 seconds, or accommodation may be due to membrane changes and local accommodation.

Figure 18:
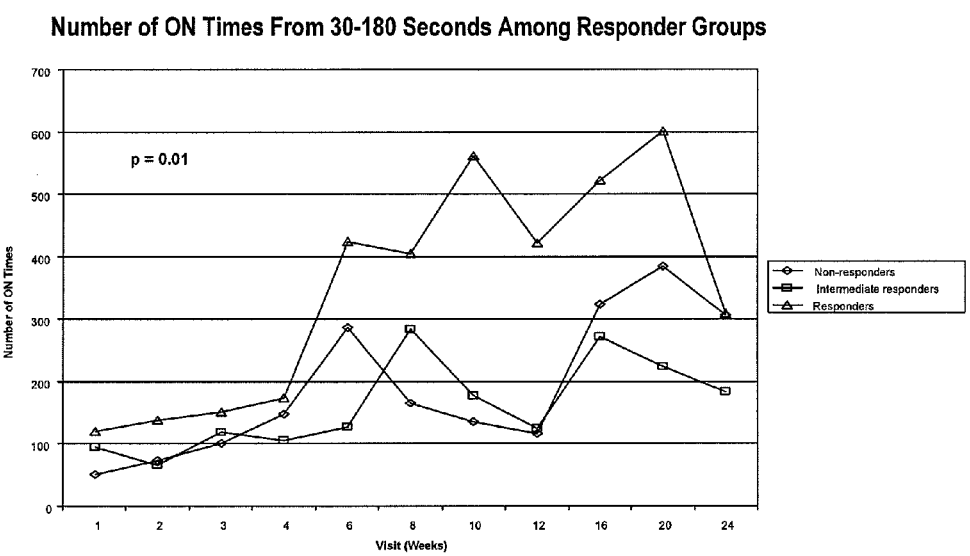
FIG. 18 is a graph illustrating patient response to the number of ON times experienced between follow-ups.

In addition to a preferred ON time of 30 seconds to 180 seconds, the duty cycle preferably has a short OFF time to maximize the number of initiations of such duty cycles per day. FIG. 18 graphically illustrates patient response to the therapy based on the number of ON times experienced by the patient. For FIG. 18, "ON time" means only those treatment durations between 30 to 180 seconds. If the patient experienced additional treatments of different durations (e.g., less than 30 seconds or greater than 180 seconds), those additional treatments are ignored in FIG. 18.

In FIG. 18, the horizontal axis is the number of week's post-activation of the implant. The vertical axis is the number of treatment ON times (again, defined for the purpose of FIG. 18 as between 30 and 180 seconds) experienced by the patient between follow-up visits.

It should be noted that not the same number of patients are in the data points for each horizontal axis location. Since patients are implanted over a period of time, while all patients had early follow-ups at the time of the analysis, not all such patients had later follow-ups. Therefore, there are more data for early weeks than for later weeks. This is also true for the other graphs described in this application.

In FIG. 18, patients are grouped into groupings labeled "non-responders", "intermediate responders" and "responders". For the purpose of FIG. 18, "non-responders" is defined as patients who experience an excess weight loss of less than or equal to zero (includes patients who gained weight). "Intermediate responders" is defined as patients who experience an excess weight loss greater than zero and less than or equal to 10%. "Responders" is defined as who patients experience an excess weight greater than 10%.

FIG. 18 further supports the surprising conclusion that 30 to 180 seconds is a preferred ON time of a duty cycle. Responders have many more such ON times than non-responders or intermediate responders. In addition, FIG. 18 may suggest the duty cycle should include an OFF time (period of time when a signal is not applied to the nerve) that is short in duration in order to maximize the number of such 30-to-180 second ON times per day.

The OFF time should be long enough to permit at least partial recovery of the nerve from the effect of the ON time. The data suggest that an OFF time period less than five minutes and, more preferably, less than two minutes permits partial recovery. By way of non-limiting examples, improved duty cycles may be (1) 2-minutes ON followed by 1-minute OFF followed by 2-minutes ON followed by 5 minutes OFF or (2) 1.75-minutes ON followed by 1-minute OFF followed by 2.5-minutes ON followed by 5 minutes OFF. These examples illustrate techniques to increase the number of ON times per day and also illustrate the duration of ON times need not be uniform. For example, the duration could be randomly distributed within the preferred range (30 to 180 seconds).

Specifically, the effect of blocking frequencies and recovery times on rat nerves has been studied. A rat's cervical vagus nerve or sciatic nerve was isolated to be used as a test nerve for study. Bipolar hook electrodes were placed in series on the isolated nerve. An electrode applied a neural blocking signal (e.g., a series of alternating current pulses with a frequency in excess of a threshold blocking frequency of 200 Hz). Another electrode connected the nerve to recording equipment to record neural impulses.

A blocking signal (greater than 200 Hz) was applied to the electrode for a period of time. After such period, the nerve impulses can be recorded by the third electrode. The frequency and duration of the blocking signal at the second electrode were varied to observe the effect of such variables on the recorded response at the other electrode. The amplitude of evoked fast and slow CAP waves was measured (at the other electrode) before and after applying blocking pulses of selected frequency and duration. Post-block measurements were taken at time points (e.g., 0-5, 10 and 15 minutes) after discontinuing the blocking signal.

Figure 19:
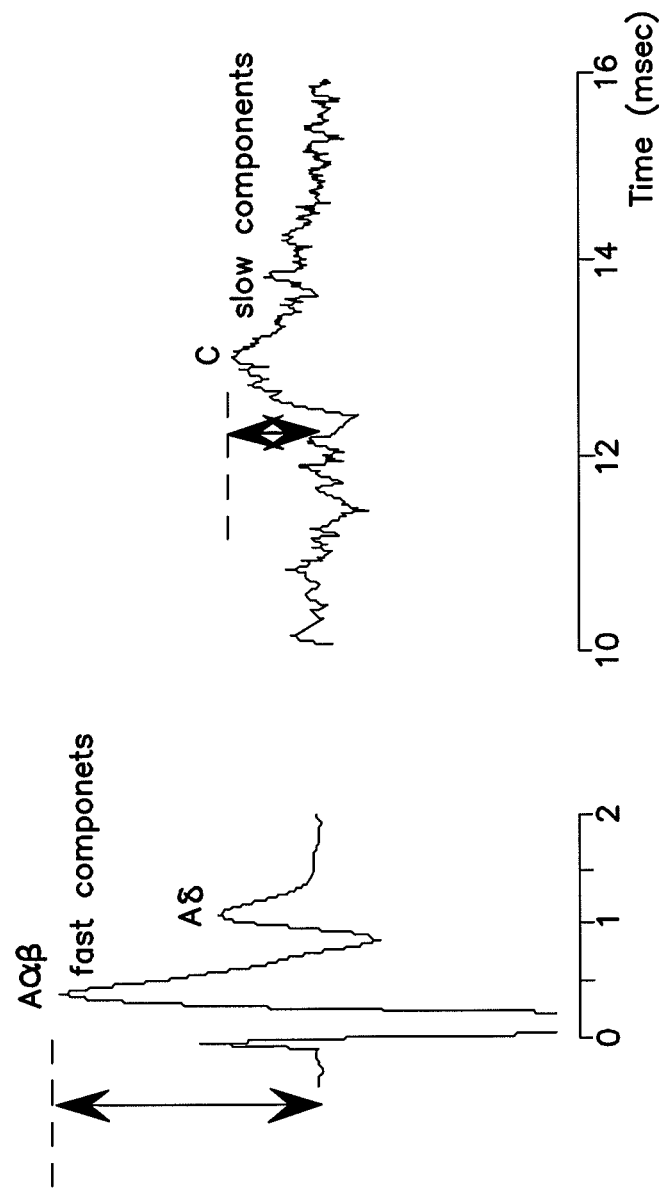
FIG. 19 shows graphs illustrating action potentials on a nerve.

The graph of FIG. 19 shows normal (i.e., not subject to a blocking frequency) nerve response to a stimulation signal (i.e., less than 200 Hz). The nerve includes three types of nerve fibers designated A$\alpha\beta$, A$\delta$ and C fibers. The A$\alpha\alpha$ and A$\delta$ fibers are myelinated while the C-fibers are not myelinated. Being myelinated, the A$\alpha\beta$ and A$\delta$ fibers have faster neural impulse propagation.

Figure 20:
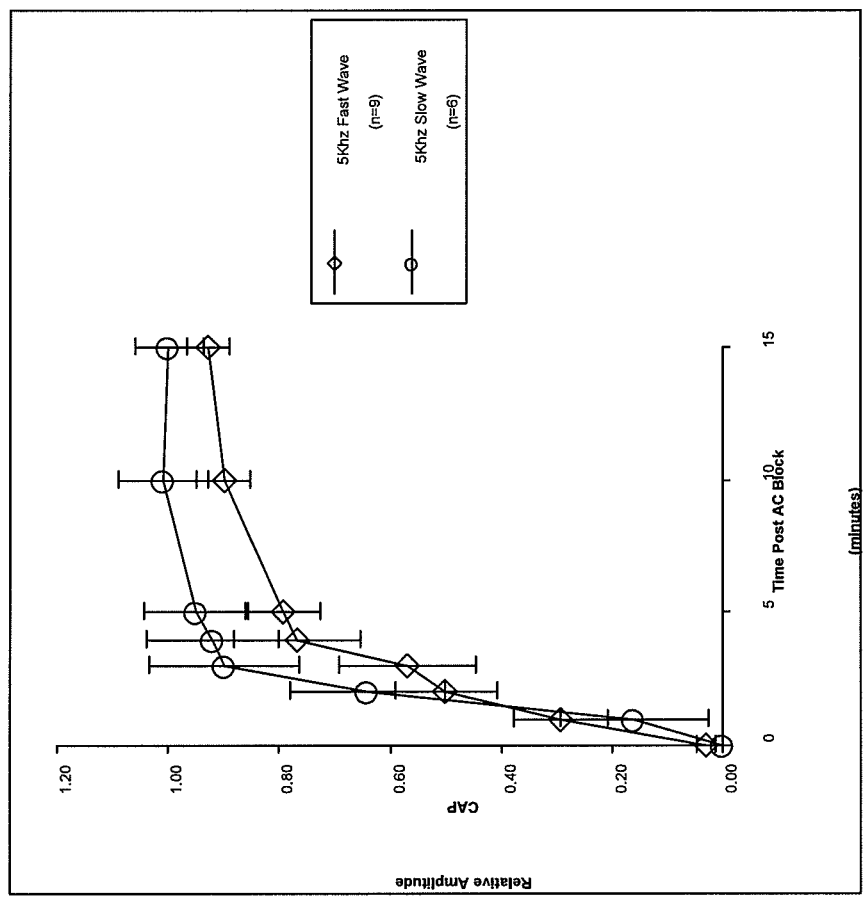
FIG. 20 is a graph illustrating recovery of a nerve following a high frequency block.

The graph of FIG. 20 shows fast and slow wave components after application of a blocking signal of 5,000 Hz for 5 minutes. FIG. 20 shows that fast and slow components were blocked at 5,000 Hz and 1 mA-4 mA. The graph also shows CAP recovery of 50% within two minutes post-block and by 90% within 10 minutes post-block.

From the above, an OFF time duration of less duration permits at least partial recovery of the nerve. Therefore, a short OFF time duration is preferred to maximize the number of ON times experienced by a patient per day while still permitting partial recovery of the nerve.

H. Ramp-Ups and Ramp-Downs

As a consequence of the shortened ON times from a target of 5-minutes, not many patients in the VBLOC-I study received any ramp-down. Only those experiencing an uninterrupted 5-minute ON time received a ramp-down. Further, patient treatments with actual ON-times less than 20-seconds in duration, never received treatment other than the mini-duty cycle ramp-up described above. Treatment durations greater than 20 seconds received a full ramp-up described above.

From the data, it was concluded that ramp-ups and ramp-downs are not beneficial from an efficacy perspective. For patients groups receiving the longest actual ON times (e.g., ">4 to 5 min" in FIG. 16), these include the only patients to receive a ramp-down. These patients experienced some of the worst efficacy correlation. Similarly, for patients for whom the ramp-up was the highest percent of the total ON time (group "0-30 sec" in FIG. 16), efficacy correlation was also poor.

With the foregoing detailed description of the present invention, it has been shown how the objects of the invention have been attained in a preferred manner. Modifications and equivalents of disclosed concepts such as those which might readily occur to one skilled in the art are intended to be included in the scope of the claims which are appended hereto. For example, while the foregoing example is described with reference to applying blocking signals to vagus nerves to treat obesity, the invention is applicable to other conditions associated with excess weight amenable to treatment by down-regulating the vagus nerve. Further, the invention is applicable to any blocking frequency applied to an autonomic nerve. Further, the invention is applicable to duty cycles for applying signals to the splanchnic nerves.

In the sections of this application pertaining to teachings of the prior art, the specification from prior art patents is substantially reproduced for ease of understanding the embodiment of the present invention. For the purpose of the present application, the accuracy of information in those patents is accepted without independent verification.

What is claimed is:

1. A method of applying a treatment to a vagus nerve in a subject having excess weight comprising:

Applying at least 10 therapy cycles to a vagus nerve of the subject having excess weight during a treatment period, wherein each therapy cycle comprises an electrical signal having parameters selected to enhance weight loss to the subject and to downregulate afferent and efferent neural activity on the vagus nerve, wherein the parameters comprise a frequency, an on period, and an off period, wherein the frequency is 300 Hz to 10,000 Hz, the on period of the electrical signal is greater than 30 seconds, and the off period is at least 1 minute and is selected to allow partial restoration of neural activity and maximize the number of on times in the treatment period, wherein the treatment period is at least eight hours;

and orally administering an effective amount of a composition comprising an effective amount of an agent selected from the group consisting of an anorexic agent, a thermogenic agent, an agent that inhibits fat absorption, an agent that enhances satiety and combinations thereof, wherein the effective amount is a dosage with fewer side effects than the recommended dosage.

2. The method according to claim 1, wherein the anorexic agent is selected from the group consisting of phentermine, fenfluramine, dexfenfluramine, endocannabinoid receptor antagonists, ghrelin antagonists, orexin antagonists, and cholecystokinin agonists.

3. The method according to claim 1, wherein the thermogenic agent is selected from the group consisting of sibutramine, leptin, leptin agonist, a leptin variant, CNTF, and a CNTF variant.

4. The method according to claim 1, wherein agent that inhibits fat absorption is orlistat or a lipin inhibitor.

5. The method according to claim 1, wherein the agent that enhances satiety is selected from the group consisting of somatostatin receptor antagonist, GLP-1 agonists, GLP-1 variants, peptide PYY, POMC agonists, neuropeptide Y inhibitors, topiramate, bupropion, naltrexone, zonisamide, amylin, amylin variants, and oxyntomodulin.

* * * * *